(12) United States Patent
Kim et al.

(10) Patent No.: US 7,514,082 B2
(45) Date of Patent: Apr. 7, 2009

(54) ANTI-VIRAL VSF PROTEIN AND HYBRIDOMA PRODUCING THE SAME

(75) Inventors: Yoon-Won Kim, Gangwon-do (KR);
Young-Jin Kim, Gangwon-do (KR);
Yo-Han Choi, Gyeongsangbuk-do (KR);
Jee-Yin Ahn, Gangwon-do (KR);
Soo-Dong Woo, Gyeonggi-do (KR);
Song-Woo Sin, Gangwon-do (KR);
Min-Kee Cho, Gangwon-do (KR);
Young-Hwan Byun, Gangwon-do (KR);
Jeung-Yul Kang, Gangwon-do (KR)

(73) Assignee: Immunemed, Inc., Gangwon-do (KR)

( * ) Notice: Subject to any disclaimer, the term of this patent is extended or adjusted under 35 U.S.C. 154(b) by 155 days.

(21) Appl. No.: 10/500,696

(22) PCT Filed: Jan. 30, 2003

(86) PCT No.: PCT/KR03/00231

§ 371 (c)(1),
(2), (4) Date: Jul. 1, 2004

(87) PCT Pub. No.: WO03/064461

PCT Pub. Date: Aug. 7, 2003

(65) Prior Publication Data

US 2005/0080236 A1    Apr. 14, 2005

(30) Foreign Application Priority Data

Feb. 1, 2002    (KR) .................. 10-2002-0005969

(51) Int. Cl.
*A61K 39/42* (2006.01)
*A61K 38/00* (2006.01)
*A61K 39/00* (2006.01)
*C12N 5/00* (2006.01)
*G01N 33/00* (2006.01)

(52) U.S. Cl. .............. 424/159.1; 424/160.1; 424/133.1; 435/325; 436/86; 514/2; 530/808

(58) Field of Classification Search ............ None
See application file for complete search history.

(56) References Cited

U.S. PATENT DOCUMENTS 5,213,795 A    5/1993    Carlson et al.

FOREIGN PATENT DOCUMENTS

WO    WO 94/23041    10/1994

OTHER PUBLICATIONS

Vlaspolder et al. Prophylaxis and therapy of virulent encephalomyocarditis virus infection in mice by monoclonal antibodies. Archives of Virology, 1988, vol. 98, 123-130.*
Cintra et al., Safety, immunogenicity and efficacy of influenza vaccine in children, 2006, Journal of Pediatrics, vol. 82, pp. 83-90.*
Barnard D., Current Status of Anti-Picornavirus Therapies, 2006, Current Pharmaceutical Design, vol. 12, pp. 1379-1390.*
Letvin N., Progress and obstacles in the development of an AIDS vaccine, 2006, Nature, vol. 6, pp. 930-939.*
Pepose et al., Ocular Herpes Simplex: Changing Epidemiology, Emerging Disease Patterns, and the Potential of Vaccine Prevention and Therapy, 2006, American Journal of Ophthalmology, pp. 547-557.*
Kim et al. "Characterization of viral inhibitory substance released from fused splenocyte" *Mol. Cells*, 7(2):165-169, 1997 (abstract only).
Suh et al. "Enhancement of VP1-specific immune responses and protection against EMCVK challenge by co-delivery of IL-12 DNA with VP1 DNA vaccine" *Vaccine*, 19:1891-1898, 2001 (abstract only).
Wood et al. "An internal ribosome binding site can be used to select for homologous recombinants at an immunolobulin heavy-chain locus" *Proc. Natl. Acad. Aci. USA*, 88(18):8006-8010, 1991.
Frolov et al., "Quantification of Endogenous Viral Polymerase, $3D^{pol}$, in Preparations of Mengo and Encephalomyocarditis Viruses," *Virology* 260(1):148-155, 1999, abstract only.
Kim et al., "Characterization of Viral Inhibitory Substance Released from Fused Splenocyte," *Mol. Cells* 7:165-169, 1997.

* cited by examiner

*Primary Examiner*—Bruce Campell
*Assistant Examiner*—Benjamin P Blumel
(74) *Attorney, Agent, or Firm*—Klarquist Sparkman, LLP

(57) ABSTRACT

Disclosed are a novel virus suppressing factor (VSF) protein having antiviral activity against a variety of viruses and a hybridoma secreting such a VSF protein. In addition, the present invention discloses a pharmaceutical composition comprising the VSF protein for prevention or treatment of viral infections in humans and animals, and a method of preventing or treating viral infections using such a pharmaceutical composition. The VSF protein has strong antiviral activity against a variety of viruses.

14 Claims, 18 Drawing Sheets

SDS-PAGE
Western blot with anti-mouse IgG
    C ; Western blot with anti-mouse gamma chain of IgG
    D ; Western blot with anti-mouse Fab of IgG 1 ; Purified VSF
2 ; Purified VSF treated with endoglycosidase 1) trypsin → IgG 1 ; Incubation for 1 hour
2 ; Incubation for 6 hour
3 ; Incubation for 24 hour

→ VSF

A. SDS-PAGE (15 %)
B. Western blot
  B-1; anti - mouse IgG (H+L)
  B-2; anti - mouse gamma chain of IgG
  B-3; anti - mouse Fab of IgG

*HM ; high range marker*
*LM ; low range marker*
*PM ; prestained high range marker*

1 ; Incubation for 1 hour
2 ; Incubation for 6 hour
3 ; Incubation for 24 hour

2) Cathepsin
→ VSF

A: SDS-PAGE
B: Western blot
   B-1: anti – mouse IgG (H+L)
   B-2: anti – mouse gamma chain of IgG
   B-3: anti – mouse Fab of IgG LM ; low marker
1: Incubation for 24 hour
2: Incubation for 48 hour
3: Incubation for 72 hour 3) Papain → Ig G                    → VSF 1. 100ng of papain
2. 1μg of papain 4) pepsin → IgG

→ VSF

1 : 100ng of pepsin
2 : 1ug of pepsin
3 : 10ug of pepsin

Heat Stability Test at 65°C

— Original VSF
— Purified VSF

SEQUENCE LISTING

<160> NUMBER OF SEQ ID NOS: 74

<210> SEQ ID NO 1
<211> LENGTH: 1401
<212> TYPE: DNA
<213> ORGANISM: mouse
<220> FEATURE:
<221> NAME/KEY: CDS
<222> LOCATION: (1)..(1401)
<223> OTHER INFORMATION: VSF H Protein

<400> SEQUENCE: 1

```
atg gga tgg agc tgg atc ttt ctc ttc ctt ctg tca gta act gca ggt        48
Met Gly Trp Ser Trp Ile Phe Leu Phe Leu Leu Ser Val Thr Ala Gly
 1               5                  10                  15 gtc cac tct gag atc cag ctg cag cag tct gga gct gag ctg gtg aag        96
Val His Ser Glu Ile Gln Leu Gln Gln Ser Gly Ala Glu Leu Val Lys
                20                  25                  30 cct ggg gct tca gtg aag ata tcc tgc aag gct tct ggt tac tca ttc       144
Pro Gly Ala Ser Val Lys Ile Ser Cys Lys Ala Ser Gly Tyr Ser Phe
            35                  40                  45 act ggc tac aac atg aac tgg gtg aag cag agc cat gga aag agc ctt       192
Thr Gly Tyr Asn Met Asn Trp Val Lys Gln Ser His Gly Lys Ser Leu
        50                  55                  60 gag tgg att gga aat att gat cct tac tat ggt agt act acc tac aat       240
Glu Trp Ile Gly Asn Ile Asp Pro Tyr Tyr Gly Ser Thr Thr Tyr Asn
 65                  70                  75                  80 cag aag ttc aag ggc aag gcc aca ttg act gta gac aaa tct tcc agc       288
Gln Lys Phe Lys Gly Lys Ala Thr Leu Thr Val Asp Lys Ser Ser Ser
                85                  90                  95 aca gcc tac atg cag ctc aac agc ctg aca tct gag gac tct gca gtc       336
Thr Ala Tyr Met Gln Leu Asn Ser Leu Thr Ser Glu Asp Ser Ala Val
               100                 105                 110 tat tac tgt gca aga gag act ggg acg agg gct atg gac tac tgg ggt       384
Tyr Tyr Cys Ala Arg Glu Thr Gly Thr Arg Ala Met Asp Tyr Trp Gly
           115                 120                 125 caa gga acc tca gtc acc gtc tcc tca gct aca aca gcc cca tct           432
Gln Gly Thr Ser Val Thr Val Ser Ser Ala Thr Thr Ala Pro Ser
       130                 135                 140
```

```
gtc tat ccc ttg gtc cct ggc tgc agt gac aca tct gga tcc tcg gtg      480
Val Tyr Pro Leu Val Pro Gly Cys Ser Asp Thr Ser Gly Ser Ser Val
145                 150                 155                 160 aca ctg gga tgc ctt gtc aaa ggc tac ttc cct gag ccg gta act gta      528
Thr Leu Gly Cys Leu Val Lys Gly Tyr Phe Pro Glu Pro Val Thr Val
                165                 170                 175 aaa tgg aac tat gga gcc ctg tcc agc ggt gtg cgc aca gtc tca tct      576
Lys Trp Asn Tyr Gly Ala Leu Ser Ser Gly Val Arg Thr Val Ser Ser
            180                 185                 190 gtc ctg cag tct ggg ttc tat tcc ctc agc agc ttg gtg act gta ccc      624
Val Leu Gln Ser Gly Phe Tyr Ser Leu Ser Ser Leu Val Thr Val Pro
        195                 200                 205 tcc agc acc tgg ccc agc cag act gtc atc tgc aac gta gcc cac cca      672
Ser Ser Thr Trp Pro Ser Gln Thr Val Ile Cys Asn Val Ala His Pro
    210                 215                 220 gcc agc aag act gag ttg atc aag aga atc gag cct aga ata ccc aag      720
Ala Ser Lys Thr Glu Leu Ile Lys Arg Ile Glu Pro Arg Ile Pro Lys
225                 230                 235                 240 ccc agt acc ccc cca ggt tct tca tgc cca cct ggt aac atc ttg ggt      768
Pro Ser Thr Pro Pro Gly Ser Ser Cys Pro Pro Gly Asn Ile Leu Gly
                245                 250                 255 gga cca tcc gtc ttc atc ttc ccc cca aag ccc aag gat gca ctc atg      816
Gly Pro Ser Val Phe Ile Phe Pro Pro Lys Pro Lys Asp Ala Leu Met
            260                 265                 270 atc tcc cta acc ccc aag gtt acg tgt gtg gtg gtg gat gtg agc gag      864
Ile Ser Leu Thr Pro Lys Val Thr Cys Val Val Val Asp Val Ser Glu
        275                 280                 285 gat gac cca gat gtc cat gtc agc tgg ttt gtg gac aac aaa gaa gta      912
Asp Asp Pro Asp Val His Val Ser Trp Phe Val Asp Asn Lys Glu Val
    290                 295                 300 cac aca gcc tgg aca cag ccc cgt gaa gct cag tac aac agt acc ttc      960
His Thr Ala Trp Thr Gln Pro Arg Glu Ala Gln Tyr Asn Ser Thr Phe
305                 310                 315                 320 cga gtg gtc agt gcc ctc ccc atc cag cac cag gac tgg atg agg ggc     1008
Arg Val Val Ser Ala Leu Pro Ile Gln His Gln Asp Trp Met Arg Gly
                325                 330                 335 aag gag ttc aaa tgc aag gtc aac aac aaa gcc ctc cca gcc ccc atc     1056
Lys Glu Phe Lys Cys Lys Val Asn Asn Lys Ala Leu Pro Ala Pro Ile
            340                 345                 350 gag aga acc atc tca aaa ccc aaa gga aga gcc cag aca cct caa gta     1104
Glu Arg Thr Ile Ser Lys Pro Lys Gly Arg Ala Gln Thr Pro Gln Val
        355                 360                 365 tac acc ata ccc cca cct cgt gaa caa atg tcc aag aag aag gtt agt     1152
Tyr Thr Ile Pro Pro Pro Arg Glu Gln Met Ser Lys Lys Lys Val Ser
    370                 375                 380 ctg acc tgc ctg gtc acc aac ttc ttc tct gaa gcc atc agt gtg gag     1200
Leu Thr Cys Leu Val Thr Asn Phe Phe Ser Glu Ala Ile Ser Val Glu
385                 390                 395                 400 tgg gaa agg aac gga gaa ctg gag cag gat tac aag aac act cca ccc     1248
Trp Glu Arg Asn Gly Glu Leu Glu Gln Asp Tyr Lys Asn Thr Pro Pro
                405                 410                 415 atc ctg gac tca gat ggg acc tac ttc ctc tac agc aag ctc act gtg     1296
Ile Leu Asp Ser Asp Gly Thr Tyr Phe Leu Tyr Ser Lys Leu Thr Val
            420                 425                 430 gat aca gac agt tgg ttg caa gga gaa att ttt acc tgc tcc gtg gtg     1344
Asp Thr Asp Ser Trp Leu Gln Gly Glu Ile Phe Thr Cys Ser Val Val
        435                 440                 445 cat gag gct ctc cat aac cac cac aca cag aag aac ctg tct cgc tcc     1392
His Glu Ala Leu His Asn His His Thr Gln Lys Asn Leu Ser Arg Ser
```

| | | | |
|---|---|---|---|
| 450 | 455 | 460 | |
| cct ggt aaa | | | 1401 |
| Pro Gly Lys | | | |
| 465 | | | |

<210> SEQ ID NO 2
<211> LENGTH: 467
<212> TYPE: PRT
<213> ORGANISM: mouse

<400> SEQUENCE: 2

Met Gly Trp Ser Trp Ile Phe Leu Phe Leu Leu Ser Val Thr Ala Gly
1               5                   10                  15

Val His Ser Glu Ile Gln Leu Gln Gln Ser Gly Ala Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly Asn Ile Asp Pro Tyr Tyr Gly Ser Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Glu Thr Gly Thr Arg Ala Met Asp Tyr Trp Gly
        115                 120                 125

Gln Gly Thr Ser Val Thr Val Ser Ser Ala Thr Thr Ala Pro Ser
    130                 135                 140

Val Tyr Pro Leu Val Pro Gly Cys Ser Asp Thr Ser Gly Ser Ser Val
145                 150                 155                 160

Thr Leu Gly Cys Leu Val Lys Gly Tyr Phe Pro Glu Pro Val Thr Val
                165                 170                 175

Lys Trp Asn Tyr Gly Ala Leu Ser Ser Gly Val Arg Thr Val Ser Ser
            180                 185                 190

Val Leu Gln Ser Gly Phe Tyr Ser Leu Ser Ser Leu Val Thr Val Pro
        195                 200                 205

Ser Ser Thr Trp Pro Ser Gln Thr Val Ile Cys Asn Val Ala His Pro
    210                 215                 220

Ala Ser Lys Thr Glu Leu Ile Lys Arg Ile Glu Pro Arg Ile Pro Lys
225                 230                 235                 240

Pro Ser Thr Pro Pro Gly Ser Ser Cys Pro Pro Gly Asn Ile Leu Gly
                245                 250                 255

Gly Pro Ser Val Phe Ile Phe Pro Pro Lys Pro Lys Asp Ala Leu Met
            260                 265                 270

Ile Ser Leu Thr Pro Lys Val Thr Cys Val Val Val Asp Val Ser Glu
        275                 280                 285

Asp Asp Pro Asp Val His Val Ser Trp Phe Val Asp Asn Lys Glu Val
    290                 295                 300

His Thr Ala Trp Thr Gln Pro Arg Glu Ala Gln Tyr Asn Ser Thr Phe
305                 310                 315                 320

Arg Val Val Ser Ala Leu Pro Ile Gln His Gln Asp Trp Met Arg Gly
                325                 330                 335

Lys Glu Phe Lys Cys Lys Val Asn Asn Lys Ala Leu Pro Ala Pro Ile
            340                 345                 350

-continued

```
Glu Arg Thr Ile Ser Lys Pro Lys Gly Arg Ala Gln Thr Pro Gln Val
        355                 360                 365
Tyr Thr Ile Pro Pro Arg Glu Gln Met Ser Lys Lys Val Ser
    370                 375                 380
Leu Thr Cys Leu Val Thr Asn Phe Phe Ser Glu Ala Ile Ser Val Glu
385                 390                 395                 400
Trp Glu Arg Asn Gly Glu Leu Glu Gln Asp Tyr Lys Asn Thr Pro Pro
                405                 410                 415
Ile Leu Asp Ser Asp Gly Thr Tyr Phe Leu Tyr Ser Lys Leu Thr Val
            420                 425                 430
Asp Thr Asp Ser Trp Leu Gln Gly Glu Ile Phe Thr Cys Ser Val Val
        435                 440                 445
His Glu Ala Leu His Asn His His Thr Gln Lys Asn Leu Ser Arg Ser
    450                 455                 460
Pro Gly Lys
465
```

<210> SEQ ID NO 3
<211> LENGTH: 702
<212> TYPE: DNA
<213> ORGANISM: mouse
<220> FEATURE:
<221> NAME/KEY: CDS
<222> LOCATION: (1)..(702)
<223> OTHER INFORMATION: VSF L3 Protein

<400> SEQUENCE: 3

```
atg agt gtg ccc act cag gtc ctg ggg ttg ctg ctg ctg tgg ctt aca      48
Met Ser Val Pro Thr Gln Val Leu Gly Leu Leu Leu Leu Trp Leu Thr
  1               5                  10                  15 ggt gcc aga tgt gac atc cag atg act cag tct cca gcc tcc cta tct      96
Gly Ala Arg Cys Asp Ile Gln Met Thr Gln Ser Pro Ala Ser Leu Ser
             20                  25                  30 gca tct gtg gga gaa act gtc acc atg aca tgt cga gca agt gag aat     144
Ala Ser Val Gly Glu Thr Val Thr Met Thr Cys Arg Ala Ser Glu Asn
         35                  40                  45 att tac agt aat tta gca tgg tat cag cag aaa cag gga aaa tct cct     192
Ile Tyr Ser Asn Leu Ala Trp Tyr Gln Gln Lys Gln Gly Lys Ser Pro
     50                  55                  60 cag ctc ctg gtc tat gtt gca aca aac tta gca gat ggt gtg cca tca     240
Gln Leu Leu Val Tyr Val Ala Thr Asn Leu Ala Asp Gly Val Pro Ser
 65                  70                  75                  80 agg ttc agt ggc agt gga tca ggc aca cag ttt tct ctg aag atc aac     288
Arg Phe Ser Gly Ser Gly Ser Gly Thr Gln Phe Ser Leu Lys Ile Asn
                 85                  90                  95 agc ctg cag cct gaa gat ttt ggg agt tat tac tgt caa cat ttt tat     336
Ser Leu Gln Pro Glu Asp Phe Gly Ser Tyr Tyr Cys Gln His Phe Tyr
            100                 105                 110 ggt tct cct cgg acg ttc ggt gga ggc acc aag ctg gaa atc aaa cgg     384
Gly Ser Pro Arg Thr Phe Gly Gly Gly Thr Lys Leu Glu Ile Lys Arg
        115                 120                 125 gct gat gct gca cca act gta tcc atc ttc cca cca tcc agt gag cag     432
Ala Asp Ala Ala Pro Thr Val Ser Ile Phe Pro Pro Ser Ser Glu Gln
    130                 135                 140 tta aca tct gga ggt gcc tca gtc gtg tgc ttc ttg aac aac ttc tac     480
Leu Thr Ser Gly Gly Ala Ser Val Val Cys Phe Leu Asn Asn Phe Tyr
145                 150                 155                 160 ccc aga gac atc aat gtc aag tgg aag att gat ggc agt gaa cga caa     528
Pro Arg Asp Ile Asn Val Lys Trp Lys Ile Asp Gly Ser Glu Arg Gln
```

```
                       165                 170                 175
aat ggt gtc ctg aac agt tgg act gat cag gac agc aaa gac agc acc           576
Asn Gly Val Leu Asn Ser Trp Thr Asp Gln Asp Ser Lys Asp Ser Thr
                180                 185                 190 tac agc atg agc agc acc ctc aca ttg acc aag gac gag tat gaa cga           624
Tyr Ser Met Ser Ser Thr Leu Thr Leu Thr Lys Asp Glu Tyr Glu Arg
            195                 200                 205 cat aac aac tat acc tgt gag gcc act cac aag aca tca act tca ccc           672
His Asn Asn Tyr Thr Cys Glu Ala Thr His Lys Thr Ser Thr Ser Pro
        210                 215                 220 atc gtc aag agc ttc aac agg aat gag tgt                                   702
Ile Val Lys Ser Phe Asn Arg Asn Glu Cys
225                 230
```

<210> SEQ ID NO 4
<211> LENGTH: 234
<212> TYPE: PRT
<213> ORGANISM: mouse

<400> SEQUENCE: 4

```
Met Ser Val Pro Thr Gln Val Leu Gly Leu Leu Leu Leu Trp Leu Thr
 1               5                  10                  15

Gly Ala Arg Cys Asp Ile Gln Met Thr Gln Ser Pro Ala Ser Leu Ser
            20                  25                  30

Ala Ser Val Gly Glu Thr Val Thr Met Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Val Ala Thr Asn Leu Ala Asp Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys His Phe Tyr
            100                 105                 110

Gly Ser Pro Arg Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Asn Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 5
<211> LENGTH: 22
<212> TYPE: DNA
<213> ORGANISM: Artificial Sequence
<220> FEATURE:
<223> OTHER INFORMATION: Primer

```
<400> SEQUENCE: 5 cagcaccttacacctaccagag                                                  22

<210> SEQ ID NO 6
<211> LENGTH: 20
<212> TYPE: DNA
<213> ORGANISM: Artificial Sequence
<220> FEATURE:
<223> OTHER INFORMATION: P

<400> SEQUENCE: 6 ctggaagtctgtcatagagg                                                    20

<210> SEQ ID NO 7
<211> LENGTH: 20
<212> TYPE: DNA
<213> ORGANISM: Artificial Sequence
<220> FEATURE:
<223> OTHER INFORMATION: P

<400> SEQUENCE: 7 gcagctatggcaactgttcc                                                    20

<210> SEQ ID NO 8
<211> LENGTH: 22
<212> TYPE: DNA
<213> ORGANISM: Artificial Sequence
<220> FEATURE:
<223> OTHER INFORMATION: P

<400> SEQUENCE: 8 ggaagacacagattccatggtg                                                  22

<210> SEQ ID NO 9
<211> LENGTH: 20
<212> TYPE: DNA
<213> ORGANISM: Artificial Sequence
<220> FEATURE:
<223> OTHER INFORMATION: P

<400> SEQUENCE: 9 atgtacagcatgcagctcgc                                                    20

<210> SEQ ID NO 10
<211> LENGTH: 21
<212> TYPE: DNA
<213> ORGANISM: Artificial Sequence
<220> FEATURE:
<223> OTHER INFORMATION: P

<400> SEQUENCE: 10 gagggcttgttgagatgatgc                                                   21

<210> SEQ ID NO 11
<211> LENGTH: 23
<212> TYPE: DNA
<213> ORGANISM: Artificial Sequence
<220> FEATURE:
<223> OTHER INFORMATION: P

<400> SEQUENCE: 11 atggttcttgccagctctaccac                                                 23

<210> SEQ ID NO 12
<211> LENGTH: 22
```

```
<212> TYPE: DNA
<213> ORGANISM: Artificial Sequence
<220> FEATURE:
<223> OTHER INFORMATION: P

<400> SEQUENCE: 12
ttaacattcc acggttccac gg                                              22

<210> SEQ ID NO 13
<211> LENGTH: 22
<212> TYPE: DNA
<213> ORGANISM: Artificial Sequence
<220> FEATURE:
<223> OTHER INFORMATION: P

<400> SEQUENCE: 13
atgggtctca accccccagct ag                                             22

<210> SEQ ID NO 14
<211> LENGTH: 22
<212> TYPE: DNA
<213> ORGANISM: Artificial Sequence
<220> FEATURE:
<223> OTHER INFORMATION: P

<400> SEQUENCE: 14
gatgctcttt aggctttcca gg                                              22

<210> SEQ ID NO 15
<211> LENGTH: 20
<212> TYPE: DNA
<213> ORGANISM: Artificial Sequence
<220> FEATURE:
<223> OTHER INFORMATION: P

<400> SEQUENCE: 15
cagagtcatg agaaggatgc                                                 20

<210> SEQ ID NO 16
<211> LENGTH: 23
<212> TYPE: DNA
<213> ORGANISM: Artificial Sequence
<220> FEATURE:
<223> OTHER INFORMATION: P

<400> SEQUENCE: 16
tcagccttcc attgcccact ctg                                             23

<210> SEQ ID NO 17
<211> LENGTH: 20
<212> TYPE: DNA
<213> ORGANISM: Artificial Sequence
<220> FEATURE:
<223> OTHER INFORMATION: P

<400> SEQUENCE: 17
gaagttcctc tctgcaagag                                                 20

<210> SEQ ID NO 18
<211> LENGTH: 22
<212> TYPE: DNA
<213> ORGANISM: Artificial Sequence
<220> FEATURE:
<223> OTHER INFORMATION: P

<400> SEQUENCE: 18
```
ctaggtttgc cgagtagatc tc                                          22

<210> SEQ ID NO 19
<211> LENGTH: 22
<212> TYPE: DNA
<213> ORGANISM: Artificial Sequence
<220> FEATURE:
<223> OTHER INFORMATION: P

<400> SEQUENCE: 19
cgcagaccat gttccatgtt tc                                          22

<210> SEQ ID NO 20
<211> LENGTH: 23
<212> TYPE: DNA
<213> ORGANISM: Artificial Sequence
<220> FEATURE:
<223> OTHER INFORMATION: P

<400> SEQUENCE: 20
ggaggttgtt actacatgtc ctg                                         23

<210> SEQ ID NO 21
<211> LENGTH: 21
<212> TYPE: DNA
<213> ORGANISM: Artificial Sequence
<220> FEATURE:
<223> OTHER INFORMATION: P

<400> SEQUENCE: 21
ggtgacatac atccttgcct c                                           21

<210> SEQ ID NO 22
<211> LENGTH: 20
<212> TYPE: DNA
<213> ORGANISM: Artificial Sequence
<220> FEATURE:
<223> OTHER INFORMATION: P

<400> SEQUENCE: 22
tcatggtcgg cttttctgcc                                             20

<210> SEQ ID NO 23
<211> LENGTH: 23
<212> TYPE: DNA
<213> ORGANISM: Artificial Sequence
<220> FEATURE:
<223> OTHER INFORMATION: P

<400> SEQUENCE: 23
atgcctggct cagcactgct atg                                         23

<210> SEQ ID NO 24
<211> LENGTH: 21
<212> TYPE: DNA
<213> ORGANISM: Artificial Sequence
<220> FEATURE:
<223> OTHER INFORMATION: P

<400> SEQUENCE: 24
catggccttg tagacacctt g                                           21

<210> SEQ ID NO 25
<211> LENGTH: 22
<212> TYPE: DNA
<213> ORGANISM: Artificial Sequence

```
<220> FEATURE:
<223> OTHER INFORMATION: P

<400> SEQUENCE: 25
atgaactgtg tttgtcgcct gg                                              22

<210> SEQ ID NO 26
<211> LENGTH: 20
<212> TYPE: DNA
<213> ORGANISM: Artificial Sequence
<220> FEATURE:
<223> OTHER INFORMATION: P

<400> SEQUENCE: 26
tcccgagtca cagtcgagtc                                                 20

<210> SEQ ID NO 27
<211> LENGTH: 24
<212> TYPE: DNA
<213> ORGANISM: Artificial Sequence
<220> FEATURE:
<223> OTHER INFORMATION: P

<400> SEQUENCE: 27
atgtgtcaat cacgctacct cctc                                            24

<210> SEQ ID NO 28
<211> LENGTH: 20
<212> TYPE: DNA
<213> ORGANISM: Artificial Sequence
<220> FEATURE:
<223> OTHER INFORMATION: p

<400> SEQUENCE: 28
tcaggcggag ctcagatagc                                                 20

<210> SEQ ID NO 29
<211> LENGTH: 21
<212> TYPE: DNA
<213> ORGANISM: Artificial Sequence
<220> FEATURE:
<223> OTHER INFORMATION: p

<400> SEQUENCE: 29
atgtgtcctc agaagctaac c                                               21

<210> SEQ ID NO 30
<211> LENGTH: 20
<212> TYPE: DNA
<213> ORGANISM: Artificial Sequence
<220> FEATURE:
<223> OTHER INFORMATION: p

<400> SEQUENCE: 30
atcctaggat cggaccctgc                                                 20

<210> SEQ ID NO 31
<211> LENGTH: 20
<212> TYPE: DNA
<213> ORGANISM: Artificial Sequence
<220> FEATURE:
<223> OTHER INFORMATION: p

<400> SEQUENCE: 31
ttcatggcgc tctgggtgac                                                 20
```

<210> SEQ ID NO 32
<211> LENGTH: 20
<212> TYPE: DNA
<213> ORGANISM: Artificial Sequence
<220> FEATURE:
<223> OTHER INFORMATION: p

<400> SEQUENCE: 32
tcattagaag gggccgtggc                                               20

<210> SEQ ID NO 33
<211> LENGTH: 22
<212> TYPE: DNA
<213> ORGANISM: Artificial Sequence
<220> FEATURE:
<223> OTHER INFORMATION: p

<400> SEQUENCE: 33
gaggaataca tccatctcgt gc                                            22

<210> SEQ ID NO 34
<211> LENGTH: 22
<212> TYPE: DNA
<213> ORGANISM: Artificial Sequence
<220> FEATURE:
<223> OTHER INFORMATION: p

<400> SEQUENCE: 34
cagtcaggac gtgttgatga ac                                            22

<210> SEQ ID NO 35
<211> LENGTH: 21
<212> TYPE: DNA
<213> ORGANISM: Artificial Sequence
<220> FEATURE:
<223> OTHER INFORMATION: p

<400> SEQUENCE: 35
cacggttcac agagtgtttc c                                             21

<210> SEQ ID NO 36
<211> LENGTH: 20
<212> TYPE: DNA
<213> ORGANISM: Artificial Sequence
<220> FEATURE:
<223> OTHER INFORMATION: p

<400> SEQUENCE: 36
ctatgagtct gcagaagctg                                               20

<210> SEQ ID NO 37
<211> LENGTH: 20
<212> TYPE: DNA
<213> ORGANISM: Artificial Sequence
<220> FEATURE:
<223> OTHER INFORMATION: p

<400> SEQUENCE: 37
atgagtccag ggagagcttc                                               20

<210> SEQ ID NO 38
<211> LENGTH: 22
<212> TYPE: DNA
<213> ORGANISM: Artificial Sequence
<220> FEATURE:
<223> OTHER INFORMATION: p

```
<400> SEQUENCE: 38
ttaggctgcc tggcggacaa tc                                    22

<210> SEQ ID NO 39
<211> LENGTH: 21
<212> TYPE: DNA
<213> ORGANISM: Artificial Sequence
<220> FEATURE:
<223> OTHER INFORMATION: p

<400> SEQUENCE: 39
atggctgcca tgtcagaaga c                                     21

<210> SEQ ID NO 40
<211> LENGTH: 23
<212> TYPE: DNA
<213> ORGANISM: Artificial Sequence
<220> FEATURE:
<223> OTHER INFORMATION: p

<400> SEQUENCE: 40
gcatcatctt cctttggca agc                                    23

<210> SEQ ID NO 41
<211> LENGTH: 21
<212> TYPE: DNA
<213> ORGANISM: Artificial Sequence
<220> FEATURE:
<223> OTHER INFORMATION: p

<400> SEQUENCE: 41
atggctcaac tttctgccca g                                     21

<210> SEQ ID NO 42
<211> LENGTH: 21
<212> TYPE: DNA
<213> ORGANISM: Artificial Sequence
<220> FEATURE:
<223> OTHER INFORMATION: p

<400> SEQUENCE: 42
ctaggccaag tggtgcagag c                                     21

<210> SEQ ID NO 43
<211> LENGTH: 20
<212> TYPE: DNA
<213> ORGANISM: Artificial Sequence
<220> FEATURE:
<223> OTHER INFORMATION: p

<400> SEQUENCE: 43
tgaggaggat gtggctgcag                                       20

<210> SEQ ID NO 44
<211> LENGTH: 21
<212> TYPE: DNA
<213> ORGANISM: Artificial Sequence
<220> FEATURE:
<223> OTHER INFORMATION: p

<400> SEQUENCE: 44
gcttcctcat ttttggactg g                                     21

<210> SEQ ID NO 45
```

```
<211> LENGTH: 23
<212> TYPE: DNA
<213> ORGANISM: Artificial Sequence
<220> FEATURE:
<223> OTHER INFORMATION: p

<400> SEQUENCE: 45
atgagcacag aaagcatgat ccg                                              23

<210> SEQ ID NO 46
<211> LENGTH: 20
<212> TYPE: DNA
<213> ORGANISM: Artificial Sequence
<220> FEATURE:
<223> OTHER INFORMATION: p

<400> SEQUENCE: 46
cttcacagag caatgactcc                                                  20

<210> SEQ ID NO 47
<211> LENGTH: 20
<212> TYPE: DNA
<213> ORGANISM: Artificial Sequence
<220> FEATURE:
<223> OTHER INFORMATION: p

<400> SEQUENCE: 47
atgacactgc tcggccgtct                                                  20

<210> SEQ ID NO 48
<211> LENGTH: 22
<212> TYPE: DNA
<213> ORGANISM: Artificial Sequence
<220> FEATURE:
<223> OTHER INFORMATION: p

<400> SEQUENCE: 48
gaatctacag tgcaaaggct cc                                               22

<210> SEQ ID NO 49
<211> LENGTH: 21
<212> TYPE: DNA
<213> ORGANISM: Artificial Sequence
<220> FEATURE:
<223> OTHER INFORMATION: p

<400> SEQUENCE: 49
cataatggct aggcccttttg c                                               21

<210> SEQ ID NO 50
<211> LENGTH: 21
<212> TYPE: DNA
<213> ORGANISM: Artificial Sequence
<220> FEATURE:
<223> OTHER INFORMATION: p

<400> SEQUENCE: 50
tcactccttc tcctcactca g                                                21

<210> SEQ ID NO 51
<211> LENGTH: 22
<212> TYPE: DNA
<213> ORGANISM: Artificial Sequence
<220> FEATURE:
<223> OTHER INFORMATION: p

<400> SEQUENCE: 51
```
atgaacaaca ggtggatcct cc                                             22

<210> SEQ ID NO 52
<211> LENGTH: 21
<212> TYPE: DNA
<213> ORGANISM: Artificial Sequence
<220> FEATURE:
<223> OTHER INFORMATION: p

<400> SEQUENCE: 52
ctgacaggtc ttcagttttg g                                              21

<210> SEQ ID NO 53
<211> LENGTH: 21
<212> TYPE: DNA
<213> ORGANISM: Artificial Sequence
<220> FEATURE:
<223> OTHER INFORMATION: p

<400> SEQUENCE: 53
atgaacgcta cacactgcat c                                              21

<210> SEQ ID NO 54
<211> LENGTH: 20
<212> TYPE: DNA
<213> ORGANISM: Artificial Sequence
<220> FEATURE:
<223> OTHER INFORMATION: p

<400> SEQUENCE: 54
tcagcagcga ctccttttcc                                                20

<210> SEQ ID NO 55
<211> LENGTH: 20
<212> TYPE: DNA
<213> ORGANISM: Artificial Sequence
<220> FEATURE:
<223> OTHER INFORMATION: p

<400> SEQUENCE: 55
gcgctcactg ctcttgtgac                                                20

<210> SEQ ID NO 56
<211> LENGTH: 20
<212> TYPE: DNA
<213> ORGANISM: Artificial Sequence
<220> FEATURE:
<223> OTHER INFORMATION: p

<400> SEQUENCE: 56
ttcagctgca cttgcaggag                                                20

<210> SEQ ID NO 57
<211> LENGTH: 21
<212> TYPE: DNA
<213> ORGANISM: Artificial Sequence
<220> FEATURE:
<223> OTHER INFORMATION: p

<400> SEQUENCE: 57
atgaagatct ctgcagctgc c                                              21

<210> SEQ ID NO 58
<211> LENGTH: 21
<212> TYPE: DNA

<210> SEQ ID NO 59
<211> LENGTH: 20
<212> TYPE: DNA
<213> ORGANISM: Artificial Sequence
<220> FEATURE:
<223> OTHER INFORMATION: p

<400> SEQUENCE: 58
cctctatcct agctcatctc c                                    21

<210> SEQ ID NO 59
<211> LENGTH: 20
<212> TYPE: DNA
<213> ORGANISM: Artificial Sequence
<220> FEATURE:
<223> OTHER INFORMATION: p

<400> SEQUENCE: 59
atgaaggtct ccaccactgc                                      20

<210> SEQ ID NO 60
<211> LENGTH: 20
<212> TYPE: DNA
<213> ORGANISM: Artificial Sequence
<220> FEATURE:
<223> OTHER INFORMATION: p

<400> SEQUENCE: 60
ctcaggcatt cagttccagg                                      20

<210> SEQ ID NO 61
<211> LENGTH: 20
<212> TYPE: DNA
<213> ORGANISM: Artificial Sequence
<220> FEATURE:
<223> OTHER INFORMATION: p

<400> SEQUENCE: 61
atgaagctct gcgtgtctgc                                      20

<210> SEQ ID NO 62
<211> LENGTH: 20
<212> TYPE: DNA
<213> ORGANISM: Artificial Sequence
<220> FEATURE:
<223> OTHER INFORMATION: p

<400> SEQUENCE: 62
ctggagctgc tcagttcaac                                      20

<210> SEQ ID NO 63
<211> LENGTH: 22
<212> TYPE: DNA
<213> ORGANISM: Artificial Sequence
<220> FEATURE:
<223> OTHER INFORMATION: p

<400> SEQUENCE: 63
atgaagcctt ttcatactgc cc                                   22

<210> SEQ ID NO 64
<211> LENGTH: 22
<212> TYPE: DNA
<213> ORGANISM: Artificial Sequence
<220> FEATURE:
<223> OTHER INFORMATION: p

<400> SEQUENCE: 64
gttattgttt gtaggtccgt gg                                   22

<210> SEQ ID NO 65
<211> LENGTH: 22
<212> TYPE: DNA
<213> ORGANISM: Artificial Sequence
<220> FEATURE:
<223> OTHER INFORMATION: p

<400> SEQUENCE: 65
atgcaggtcc ctgtcatgct tc                                          22

<210> SEQ ID NO 66
<211> LENGTH: 22
<212> TYPE: DNA
<213> ORGANISM: Artificial Sequence
<220> FEATURE:
<223> OTHER INFORMATION: p

<400> SEQUENCE: 66
ctagttcact gtcacactgg tc                                          22

<210> SEQ ID NO 67
<211> LENGTH: 22
<212> TYPE: DNA
<213> ORGANISM: Artificial Sequence
<220> FEATURE:
<223> OTHER INFORMATION: p

<400> SEQUENCE: 67
atgaggatct ctgccacgct tc                                          22

<210> SEQ ID NO 68
<211> LENGTH: 22
<212> TYPE: DNA
<213> ORGANISM: Artificial Sequence
<220> FEATURE:
<223> OTHER INFORMATION: p

<400> SEQUENCE: 68
cttcaaggct ttggagttgg gg                                          22

<210> SEQ ID NO 69
<211> LENGTH: 20
<212> TYPE: DNA
<213> ORGANISM: Artificial Sequence
<220> FEATURE:
<223> OTHER INFORMATION: p

<400> SEQUENCE: 69
atgaacccaa gtgctgccgt                                             20

<210> SEQ ID NO 70
<211> LENGTH: 23
<212> TYPE: DNA
<213> ORGANISM: Artificial Sequence
<220> FEATURE:
<223> OTHER INFORMATION: p

<400> SEQUENCE: 70
cagttaagga gcccttttag acc                                         23

<210> SEQ ID NO 71
<211> LENGTH: 20
<212> TYPE: DNA
<213> ORGANISM: Artificial Sequence
<220> FEATURE:

```
<223> OTHER INFORMATION: p

<400> SEQUENCE: 71
atgagacttc tcctcctgac                                                   20

<210> SEQ ID NO 72
<211> LENGTH: 20
<212> TYPE: DNA
<213> ORGANISM: Artificial Sequence
<220> FEATURE:
<223> OTHER INFORMATION: p

<400> SEQUENCE: 72
ctgttaccca gtcagggtta                                                   20

<210> SEQ ID NO 73
<211> LENGTH: 20
<212> TYPE: DNA
<213> ORGANISM: Artificial Sequence
<220> FEATURE:
<223> OTHER INFORMATION: p

<400> SEQUENCE: 73
tgatgggtgt gaaccacgag                                                   20

<210> SEQ ID NO 74
<211> LENGTH: 20
<212> TYPE: DNA
<213> ORGANISM: Artificial Sequence
<220> FEATURE:
<223> OTHER INFORMATION: p

<400> SEQUENCE: 74
cttactcctt ggaggccatg                                                   20
```

ANTI-VIRAL VSF PROTEIN AND HYBRIDOMA PRODUCING THE SAME

CROSS REFERENCE TO RELATED APPLICATIONS

This application is the § 371 U.S. National Phase of International Application No. PCT/KR03/00231, filed Jan. 30, 2003, which was published in English under PCT Article 21(2), which in turn claims the benefit of Korean Application No. 10-2002-0005969, filed Feb. 1, 2002, which is incorporated by reference herein in its entirety.

TECHNICAL FIELD

The present invention relates, in general, to a novel viral-inhibitory substance, and more particularly to a virus suppressing factor (VSF) having antiviral activity, which is produced in an immune cell infected with a variant of the encephalomyocarditis virus (EMCV), EMC-DV. In detail, the present invention relates to a VSF protein having inhibitory activity against a variety of viruses, produced in an immune cell infected with a variant of the encephalomyocarditis virus, EMC-DV, a method of paring such a VSF protein, a hybridoma secreting such a VSF protein, and a method of preparing such a hybridoma. In addition, the present invention is concerned with a pharmaceutical composition comprising the VSF protein for prevention or treatment of viral infections, and a method of preventing or treating viral infections using such a pharmaceutical composition.

BACKGROUND

The conventional antiviral agents are largely classified into synthetic chemical compounds and bio-derived molecules. The synthetic chemical compounds, which were mainly developed to act only against specific viral diseases, are disadvantageous in that they have several side effects, and viruses easily develop resistance thereto. Cytokines such as interferons (IFNs) are well known as bio-derived anti-viral agents. The cytokines differ from the synthetic compounds in terms of not having severe side effects. However, there are disadvantages to cytokines, as follows: they have limitations in their practical use and low efficacy in vivo.

On the other hand, one subject infected with HIV has been found not to develop AIDS, suggesting that his immune system has a potential mechanism to inhibit HIV function. Recently, it has been reported by scientists that virus-infected $CD8^+$ cells function to inhibit some viral functions by secreting a new soluble molecule.

After in vitro culturing $CD8^+$ cells derived from HIV-infected individuals not developing AIDS, when HIV-infected cells were treated with the culture supernatant of the $CD8^+$ cells, it was found that HIV proliferation is suppressed, and that the $CD8^+$ cells secreted a soluble antiviral substance (Walker C M et al., Science, 234, 1563-1566(1986); and Walker C M et al., Immunology, 66, 628-630 (1989)). Such a soluble antiviral substance was also discovered in SIV-infected monkeys and FIV-infected cats. In addition, it has been reported that HIV proliferation is suppressed by a soluble antiviral substance secreted by $CD8^+$ cells infected with herpes virus. This finding was very interesting in light of the fact that an antiviral substance secreted by immune cells infected with a specific virus is effective in inhibiting functions of a different virus.

Such an antiviral substance produced by $CD8^+$ cells is called '$CD8^+$ cell antiviral factor (CAF), and efforts to identify the antiviral factor and its action mechanism has been actively undertaken. CAF seems to affect target cells to induce an antiviral state, rather than to directly act on viruses. Therefore, in contrast to the conventional antiviral agents, CAF is predicted to rarely accompany unexpected side effects or generate CAF-resistant viruses.

U.S. Pat. No. 5,707,814 discloses a $CD8^+$ cell antiviral actor (CAF) having inhibitory activity against HIV, SIV and retrovirus infection, which is isolated from $CD8^+$ cell culture fluids. In International Pat. Publication No. WO99/57272, CAF is disclosed as having a molecular weight of about 8 kDa. Also, CAF isolated from eggs derived from a immunized avian is disclosed in International Pat. Publication NO. WO01/07472A1.

However, in the cases of the aforementioned disclosures, it is hard to produce in vitro $CD8^+$ cells secreting the antiviral substance CAF because $CD8^+$ cells cannot be immortalized, resulting in that CAF is secreted transiently and at a small amount in vitro. For these reasons, in vivo experiments using animals cannot be performed. Moreover, when culture fluid of cells secreting CAF is diluted up to over 10 times, the antiviral effect of CAF disappears even in vitro.

To overcome the problems encountered in the prior art, the present inventors conducted intensive and thorough research into an antiviral factor. The research, in which a cell line continuously secreting an antiviral substance was established by isolating immune cells stimulated by injection of a variant of encephalomyocarditis virus, and fusing the immune cells with myeloma cells to produce hybridomas, resulted in the finding that a VSF protein, secreted by the cell line, has strong antiviral activity against a variety of viruses. Based on the finding, the present inventors identified characteristics of the VSF protein.

DISCLOSURE OF THE INVENTION

The present invention provides a virus suppressing factor (VSF) protein having the following properties: (a) it is increasingly produced in an immune cell stimulated by a variant of encephalomyocarditis virus, EMC-DV, (b) it has antiviral activity which is unchanged by immunoprecipitation and immunoneutralization, (c) it is inactivated by proteinase K, (d) it is not one of the group of antiviral cytokines consisting of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, G-CSF, GM-CSF, TNF-α, TNF-β, IFN-α, IFN-β, IFN-γ, TGF-β, RANTES, MIP-1α, MIP-1β, MIP-1γ, MCP-1, MCP-3, IP-10 and lymphotactin, (e) it comprises about 55 kDa polypeptide (H), about 30 kDa polypeptides (L1 and L2) and about 25 kDa polypeptide (L3), and (f) it has a molecular weight of over about 100 kDa.

In addition, the present invention provides a VSF protein having the following properties: (a) it is increasingly produced in an immune cell stimulated by a variant of encephalomyocarditis virus, EMC-DV, (b) it has an antiviral activity which is unchanged by immunoprecipitation and immunoneutralization, (c) it is inactivated by proteinase K, (d) it is not one of the group of antiviral cytokines consisting of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, G-CSF, GM-CSF, TNF-α, TNF-β, IFN-α, IFN-β, IFN-γ, TGF-β, RANTES, MIP-1α, MIP-1β, MIP-1γ, MCP-1, MCP-3, IP-10 and lymphotactin, (e) it comprises about 55 kDa polypeptide (H), about 30 kDa polypeptides (L1 and L2) and about 25 kDa polypeptide (L3), (f) it has a molecular weight of over about 100 kDa, (g) the H polypeptide has a DNA sequence designated as SEQ ID NO: 1 and an amino acid sequence designated as SEQ ID NO: 2, and (h) the L3 polypeptide has a DNA sequence designated as SEQ ID NO: 3 and an amino acid sequence designated as SEQ ID NO: 4.

Preferably, the VSF protein of the present invention has antiviral activity to suppress proliferation or replication of a virus belonging to the family Orthomyxoviridae, Picornaviridae, Retroviridae or Herpes.

The present invention provides a method of producing a hybridoma, comprising fusing an immune cell stimulated by a variant of encephalomyocarditis virus, EMC-DV, with a tumor cell, and producing a hybridoma secreting a VSF protein.

The present invention provides a method of preparing a VSF protein, comprising producing a hybridoma secreting a VSF protein by fusing an immune cell stimulated by a variant of encephalomyocarditis virus, EMC-DV, with a tumor cell, culturing the hybridoma, and isolating a VSF protein from a culture fluid of the hybridoma.

In addition, the present invention provides a method of preparing a VSF protein, comprising producing a hybridoma secreting a VSF protein by fusing an immune cell stimulated by a variant of encephalomyocarditis virus, EMC-DV, with a tumor cell, injecting the hybridoma into an animal, and isolating a VSF protein from an ascitic fluid obtained from the animal.

Preferably, the VSF protein of the present invention is isolated from the culture fluid or ascitic fluid using a Blue Sepharose column, a Protein A agarose column, a hydroxyapatite resin column, a FPLC column, or sucrose gradient.

Further, the present invention provides a hybridoma producing a VSF protein, which is prepared by fusing an immune cell stimulated by a variant of encephalomyocarditis virus, EMC-DV, with a tumor cell.

Preferably, the hybridoma is a hybridoma 4D1B (accession number KCLRF-BP-00052).

Still further, the present invention provides a pharmaceutical composition for prevention and treatment of viral infections, comprising a therapeutically or preventively effective amount of a VSF protein and a pharmaceutically acceptable carrier.

Still further, the present invention provides a method of preventing and treating viral infections, comprising administering a therapeutically or preventively effective amount of a VSF protein to a subject suffering from a viral infection.

BRIEF DESCRIPTION OF THE DRAWINGS

The above and other objects, features and other advantages of the present invention will be more clearly understood from the following detailed description taken in conjunction with the accompanying drawings, in which:

Figure 2:
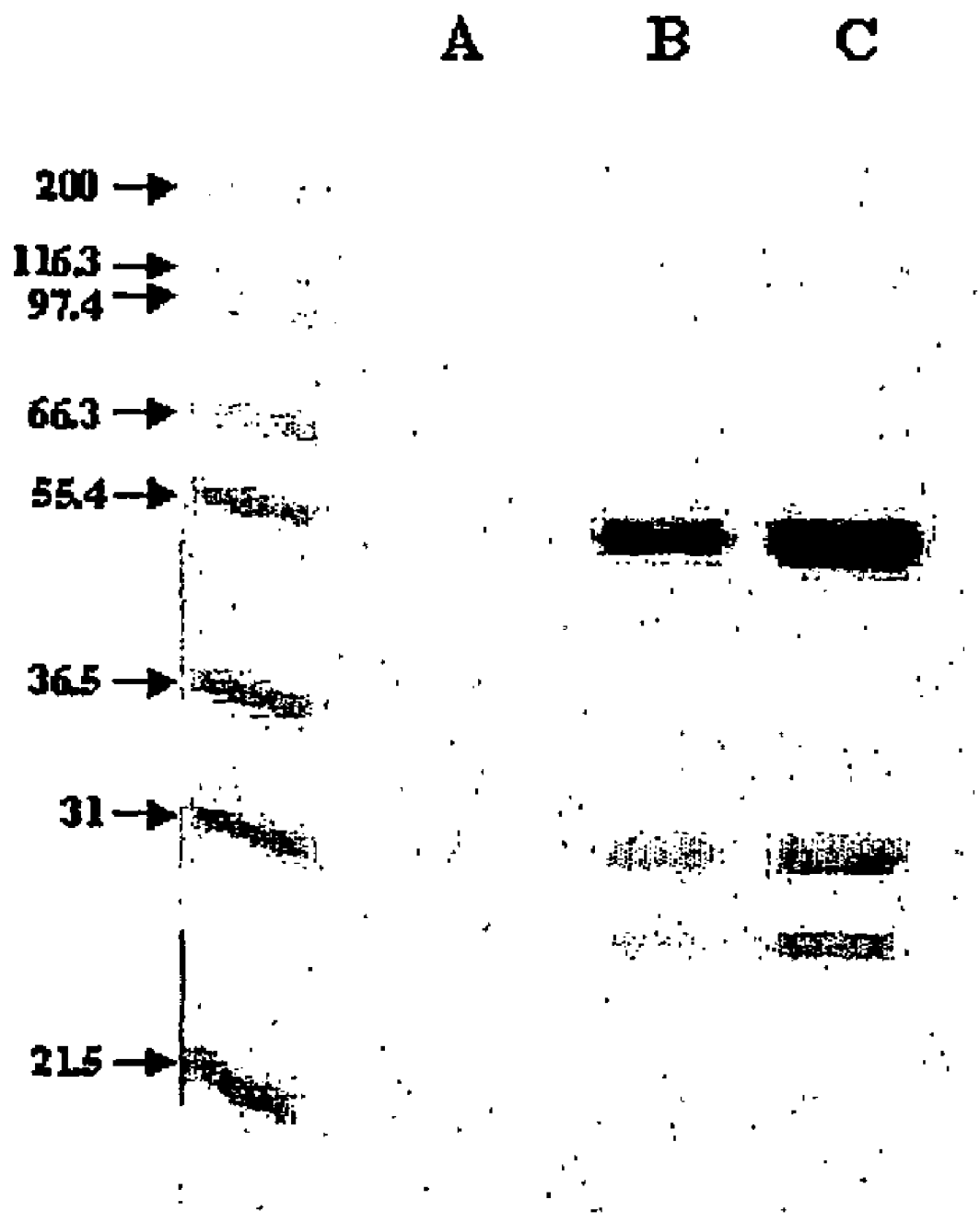

FIG. 2 is a photograph showing a result of fractionation of a VSF protein according to the present invention using Centricon membranes with various pore sizes (A: 50-100 kDa molecular weight; B: 100-500 kDa molecular weight; and C: >500 kDa molecular weight);

FIG. 6 is a graph showing antiviral activity of ascitic fluids, obtained from mice intraperitoneally administered with a hybridoma according to the present invention, against HIV-1;

FIGS. 12A to 12C are graphs showing heat stability of a VSF protein according to the present invention.

BEST MODES FOR CARRYING OUT THE INVENTION

Figure 1:
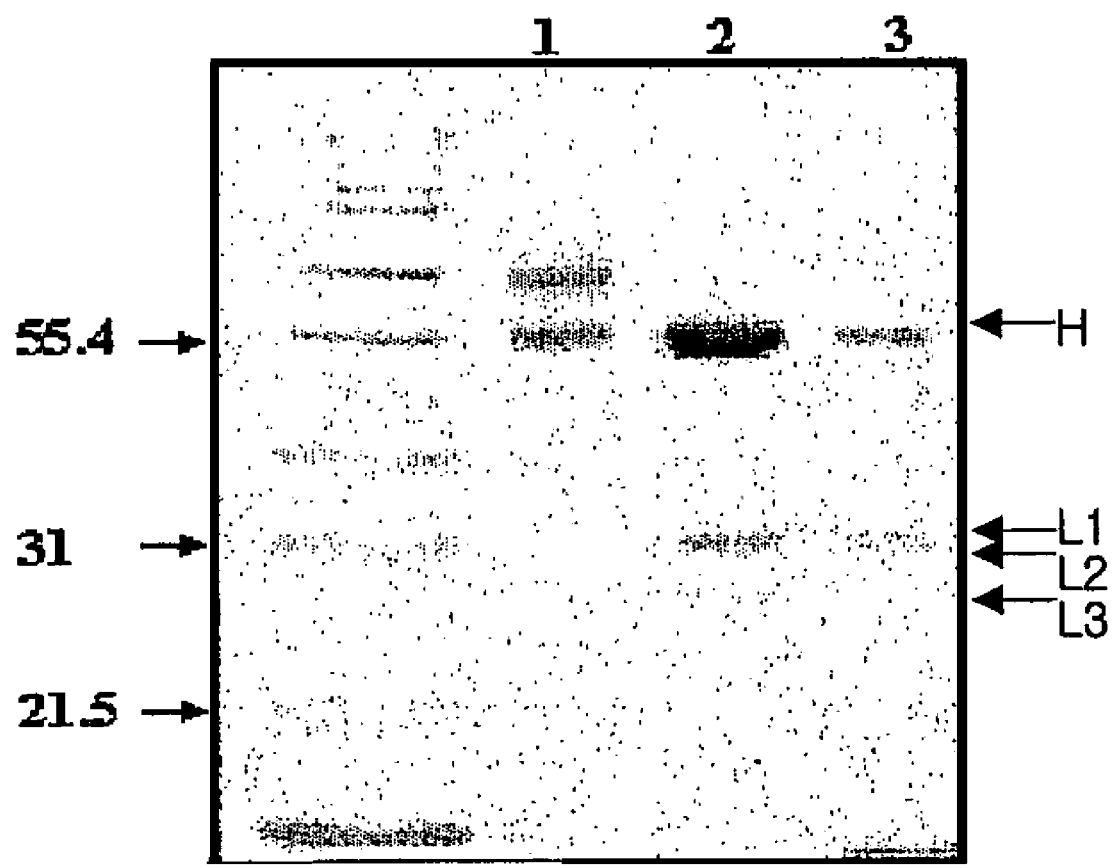
FIG. 1 is a photograph showing a result of SDS-PAGE of a VSF protein according to the present invention (lane 1: VSF purified using a hydroxyapatite resin column; lane 2: VSF purified using a Protein A agarose column; and lane 3: VSF purified using a Blue Sepharose column)

In an aspect of the present invention, there is provided a virus suppressing factor (VSF) protein having antiviral activity against a variety of viruses. Encephalomyocarditis virus (EMCV) belongs to the genus Picornaviridae (Kim Y W et al. The Journal of the Korean Society for Microbiology, 30, 671-681 (1995); and Craighead J E, Progress in Medical Virology, 19, 161-214(1975)). EMCV has various variants including the M, D, B and DV variants.

The M variant of EMCV (EMC-M variant) induces diabetes mellitus in mice at an irregular frequency, and diabetes mellitus is developed in mice infected with the D variant of EMCV (EMC-D variant) at over 90% frequency (Craighead J E and McLane M F, Science, 162, 913-914 (1968)). The B variant of EMCV (EMC-B variant) is known not to cause diabetes mellitus in nice, and can be isolated by plaque purification (Yoon J W et al., J. Gen. Virol, 69, 1085-1090 (1988)). Although the EMC-D and EMC-B variants are almost indistinguishable biochemically and immunologically, the EMC-D variant rarely induces production of IFNs, whereas the EMC-B variant induces high production of IFNs (Yoon J W et al., J. Infect Dis, 147, 155-159 (1983)). In this regard, it seems likely that diabetes mellitus is developed by production of IFNs. On the other hand, it was reported by the present inventors that the DV variant of EMCV (EMC-DV variant) rarely induces production of IFNs as well as diabetes mellitus (Kim Y W et al. The Journal of the Korean Society for Microbiology, 30, 671-681 (1995)).

Both of the EMC-D and EMC-DV variants can attach to pancreatic beta cells, and replicate and proliferate in the beta cells in vitro, finally destroying the beta cells. However, in case of in vivo infection, only the EMC-D variant is diabetogenic by infecting and destroying pancreatic beta cells, whereas, in case of the EMC-DV variant, viral replication is stopped 48 hrs after infection, and viral proteins gradually disappear. The EMC-DV variant initiates replication after infection, but the viral replication is stopped early, not destroying infected cells, resulting in no infiltration of immune cells into islets of pancreas.

The VSF protein of the present invention is a protein of which production is increased in a cell stimulated by the EMC-DV variant. The term "cell", used in the description of the cell stimulated by an EMC-DV variant, refers to an animal cell, and particularly, to an immune cell functioning to protect an individual from viral infection, reject cells derived from other individuals, and remove transformed cells and aged tissues. Preferably, the cell means an immune cell present in the spleen. Examples of the immune cell may include macrophages, granulocytes, T lymphocytes, B lymphocytes, NK cells and LAK cells. The "animal", used in the expression of the animal cell, includes livestock, which are exemplified by cattle, sheep, pigs, horses, dogs, fowls, ducks and turkeys, mammals, which are exemplified by mice, rats, hamsters and humans, as well as fishes, amphibians, reptiles, and birds, and wherein the VSF protein of the present invention displays antiviral activity in the aforementioned animals.

The term "antiviral activity", which the VSF protein of the present invention displays, refers to activity to supress proliferation or replication of a pathogenic virus, and thus reduce, inhibit or prevent a viral infection. The term "pathogenic virus", of which proliferation or replication is inhibited by the antiviral activity, refers to a virus causing a disease in an animal or a human. Examples of the pathogenic virus may include viruses belonging to the genus *Orthomyxoviridae, Picorna viridae, Retroviridae* and *Herpes*. Representative examples of the pathogenic virus may include EMC virus (EMCV), Mengo virus, influenza virus, HIV, and human cytomegalovirus (HCMV). In particular, the VSF protein of the present invention exhibits antiviral activity against Mengo virus belonging to the genus *Picornaviridae*, as well as influenza virus belonging to the genus *Orthomyxoviridae*, which has a genetic structure and life cycle completely different from EMC virus belonging to the genus *Picorna viridae* (Examples 10 to 11). In addition, the VSF protein effectively inhibits proliferation of HIV-1 belonging to the genus *Retroviridae* (Example 12), and has inhibitory effect on proliferation of vesicular stomatitis virus (VSV) (Example 23).

The antiviral VSF protein according to the present invention has the following properties.

1. The VSF protein of the present invention has physiological activity similar to that of cytokines, but has biological activity distinct from that of conventional antiviral cytokines. In particular, the VSF protein is a different kind of protein from the conventionally known antiviral cytokines including IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, G-CSF, GM-CSF, TNF-α, TNF-β, IFN-α, IFN-β, IFN-γ, TGF-β, RANTES, MIP-1α, MIP-1β, MIP-1γ, MCP-1, MCP-3, IP-10 and lymphotactin.

The present inventors performed RT-PCR to investigate expression of specific cytokines in a hybridoma secreting a VSF protein. As a result, the hybridoma according to the present invention was demonstrated not to express specifically any of the aforementioned cytokines (Example 4).

2. The VSF protein comprises several subunits, in which the subunits are associated with each other by covalent or non-covalent bonding, thereby forming a macromolecule having a molecular weight of over about 100 kDa.

Through the measurement of molecular weight of the VSF protein using Centricon™, the VSF protein was identified to be present as a macromolecule of over 100 kDa in a naturally occurring state, which is a minimum unit capable of displaying antiviral activity (Example 9), and the highest antiviral activity of the VSF protein was found in a fraction of over 500 kDa When analyzing a 163 kDa fraction, purified by using a FPLC (Fast Flow Performance Liquid Chromatography) column, by SDS-PAGE, the resulting protein pattern is identical to major bands as shown in FIG. 1, found in active fractions obtained by chromatography using three different columns (hydroxyapatite column, Protein A agarose column, and Blue Sepharose column). Therefore, an active form of the VSF protein is believed to have a molecular weight of 163 kDa.

On the other hand, when analyzing fractions obtained by performing open column chromatography (using hydroxyapatite column, Protein A agarose column, and Blue Sepharose column) and FPLC, and sucrose gradient centrifugation, by SDS-PAGE, four major bands of below 100 kDa were found, which are H (about 55 kDa), L1 (about 30 kDa), L2 (about 30 kDa) and L3 (about 25 kDa). As a result of measuring density of the bands by densitometry, ratio of H: L1: L2: L3 was 1: 0.5-1: 0.5-1: 0.5-2. Subunits of the VSF protein of the present invention are believed to associate by relatively strong bonding.

As a result of Western blotting using anti-mouse IgG(H+L) antibody and anti-mouse Fab-specific antibody, the four major bands as shown in FIG. 1 were detected. When using anti-mouse gamma heavy chain-specific antibody, only the H band (about 55 kDa) among the four major bands was detected. When using anti-mouse κ-light chain-specific antibody, three bands (L1, L2 and L3) of the four major bands were detected.

3. H and L3 subunit of the VSF protein have DNA sequences and amino acid sequences designated as SEQ ID NOs 1 to 4, as follows.

SEQ ID NO: 1: DNA Sequence of H Subunit of VSF Protein

```
ATGGGATGGAGCTGGATCTTTCTCTTCCTTCTGTCAGTAACTGCAGGTGTCCACTCT

GAGATCCAGCTGCAGCAGTCTGGAGCTGAGCTGGTGAAGCCTGGGGCTTGAGTGA

AGATATCCTGCAAGGCTTCTGGTTACTCATTCACTGGCTACAACATGAACTGGGTGA

AGCAGAGCCATGGAAAGAGCCTTGAGTGGATTGGAAATATTGATCCTTACTATGGT
```

```
AGTACTACCTACAATCAGAAGTTCAAGGGCAAGGCCACATTGACTGTAGACAAATC

TTCCAGCACAGCCTACATGCAGCTCAACAGCCTGACATCTGAGGACTCTGCAGTCT

ATTACTGTGCAAGAGAGACTGGGACGAGGGCTATGGACTACTGGGGTCAAGGAAC

CTCAGTCACCGTCTCCTCAGCTACAACAACAGCCCCATCTGTCTATCCCTTGGTCCC

TGGCTGCAGTGACACATCTGGATCCTCGGTGACACTGGGATGCCTTGTCAAAGGCT

ACTTCCCTGAGCCGGTAACTGTAAAATGGAACTATGGAGCCCTGTCCAGCGGTGTG

CGCACAGTCTCATCTGTCCTGCAGTCTGGGTTCTATTCCCTCAGCAGCTTGGTGACT

GTACCCTCCAGCACCTGGCCCAGCCAGACTGTCATCTGCAACGTAGCCCACCCAGC

CAGCAAGACTGAGTTGATCAAGAGAATCGAGCCTAGAATACCCAAGCCCAGTACC

CCCCAGGTTCTTCATGCCCACCTGGTAACATCTTGGGTGGACCATCCGTCTTCATC

TTCCCCCCAAAGCCCAAGGATGCACTCATGATCTCCCTAACCCCCAAGGTTACGTG

TGTGGTGGTGGATGTGAGCGAGGATGACCCAGATGTCCATGTCAGCTGGTTTGTGG

ACAACAAAGAAGTACACACAGCCTGGACACAGCCCCGTGAAGCTCAGTACAACA

GTACCTTCCGAGTGGTCAGTGCCCTCCCCATCCAGCACCAGGACTGGATGAGGGG

CAAGGAGTTCAAATGCAAGGTCAACAACAAAGCCCTCCCAGCCCCCATCGAGAGA

ACCATCTCAAAACCCAAAGGAAGAGCCCAGACACCTCAAGTATACACCATACCCC

CACCTCGTGAACAAATGTCCAAGAAGAAGGTTAGTCTGACCTGCCTGGTCACCAA

CTTCTTCTCTGAAGCCATCAGTGTGGAGTGGGAAAGGAACGGAGAACTGGAGCAG

GATTACAAGAACACTCCACCCATCCTGGACTCAGATGGGACCTACTTCCTCTACAG

CAAGCTCACTGTGGATACAGACAGTTGGTTGCAAGGAGAAATTTTTACCTGCTCCG

TGGTGCATGAGGCTCTCCATAACCACCACACACAGAAGAACCTGTCTCGCTCCCT

GGTAAA
```

SEQ ID NO: 2: Amino Acid Sequence of H Subunit of VSF Protein

```
MGWSWIFLFLLSVTAGVHSEIQLQQSGAELVKPGASVKISCKASGYSFTGYNMNWVK

QSHGKSLEWIGNIDPYYGSTTYNQKFKGKATLTVDKSSSTAYMQLNSLTSEDSAVYYC

ARETGTRAMDYWGQGTSVTVSSATTTAPSVYPLVPGCSDTSGSSVTLGCLVKGYFPEP

VTVKWNYGALSSGVRTVSSVLQSGFYSLSSLVTVPSSTWPSQTVICNVAHPASKTELIK

RIEPRIPKPSTPPGSSCPPGNILGGPSVFIFPPKPKDALMISLTPKVTCVVVDVSEDDPDV

HVSWFVDNKEVHTAWTQPREAQYNSTFRVVSALPIQHQDWMRGKEFKCKVNNKALP

APIERTISKPKGRAQTPQVYTIPPPREQMSKKKVSLTCLVTNFFSEAISVEWERNGELEQ

DYKNTPPILDSDGTYFLYSKLTVDTDSWLQGEIFTCSVVHEALHNHHTQKNLSRSPGK
```

SEQ ID NO: 3: DNA Sequence of L3 Subunit of VSF Protein

```
ATGAGTGTGCCCACTCAGGTCCTGGGGTTGCTGCTGCTGTGGCTTACAGGTGCCAG

ATGTGACATCCAGATGACTCAGTCTCCAGCCTCCCTATCTGCATCTGTGGGAGAAA

CTGTCACCATGACATGTCGAGCAAGTGAGAATATTTACAGTAATTTAGCATGGTATC

AGCAGAAACAGGGAAAATCTCCTCAGCTCCTGGTCTATGTTGCAACAAACTTAGCA
```

```
                                           -continued
GATGGTGTGCCATCAAGGTTCAGTGGCAGTGGATCAGGCACACAGTTTTCTCTGAA

GATCAACAGCCTGCAGCCTGAAGATTTTGGGAGTTATTACTGTCAACATTTTTATGG

TTCTCCTCGGACGTTCGGTGGAGGCACCAAGCTGGAAATCAAACGGGCTGATGCT

GCACCAACTGTATCCATCTTCCCACCATCCAGTGAGCAGTTAACATCTGGAGGTGC

CTCAGTCGTGTGCTTCTTGAACAACTTCTACCCCAGAGACATCAATGTCAAGTGGA

AGATTGATGGCAGTGAACGACAAAATGGTGTCCTGAACAGTTGGACTGATCAGGA

CAGCAAAGACAGCACCTACAGCATGAGCAGCACCCTCACATTGACCAAGGACGAG

TATGAACGACATAACAACTATACCTGTGAGGCCACTCACAAGACATCAACTTCACC

CATCGTCAAGAGCTTCAACAGGAATGAGTGT
```

SEQ ID NO: 4: Amino Acid Sequence of L3 Subunit of VSF Protein

```
MSVPTQVLGLLLLWLTGARCDIQMTQSPASLSASVGETVTMTCRASENIYSNLAWYQ

QKQGKSPQLLVYVATNLADGVPSRFSGSGSGTQFSLKINSLQPEDFGSYYCQHFYGSPR

TFGGGTKLEIKRADAAPTVSIFPPSSEQLTSGGASVVCFLNNFYPRDINVKWKIDGSER

QNGVLNSWTDQDSKDSTYSMSSTLTLTKDEYERHNNYTCEATHKTSTSPIVKSFNRNE

C
```

As a result of BLAST search for amino acid homology of a N-terminal region (137 amino acids) of the H subunit and a N-terminal region (127 amino acids) of the L3 subunit of the VSF protein, the N-terminal region of the H subunit was found to have homology with the known amino acid sequences of the variable (V) region (score: 222) of Ig heavy chain precursor, and the Ig gamma 1 heavy chain (score: 217), in addition to with the unidentified protein for MGC:19223 (score: 216). The N-terminal region of the L3 subunit has amino acid homology with Ig kappa chain (score: 206) and the V region of a Ig kappa chain precursor (score: 199), in addition to with the unidentified protein for MGC:28604 (score: 199).

4. When subjecting the VSF protein to immunoprecipitation and immunoneutralization using sheep anti-mouse IgG (H+L), antiviral activity of the VSF protein was not changed. In detail, after incubating the VSF protein of the present invention along with 100 μg of sheep anti-mouse IgG(H+L) at 4° C. overnight, and centrifuging the reaction mixture at 1000×g for 10 min, and analyzing the supernatant by a virus inhibition test (VIT), the antiviral activity of the VSF protein was found not to be changed.

5. The VSF protein did not show a band shift on a SDS-PAGE gel even after treatment of endoglycosidase. This result indicates that the VSF protein is nonglycosylated, or glycosylated at a very low level.

6. The VSF protein was evaluated for sensitivity to various proteinases. In case of being treated with papain, the heavy chain of IgG and the H subunit of the VSF protein showed different reactivity to anti-gamma. In case of being treated with pepsin, the VSF protein and IgG showed different reactivities to anti-Fab. Also, all of H, L1, L2 and L3 subunits of the VSF protein were found to be sensitive to proteinase K. When being treated with trypsin, both of heavy and light chains of mouse IgG showed weak resistance to trypsin, while, in case of the VSF protein, the H subunit was very sensitive to trypsin and thus destroyed, but the L1, L2 and L3 subunits were minimally degraded by trypsin cleavage. Further, the VSF protein was not cleaved by cathepsin.

In another aspect of the present invention, there is provided a hybridoma prepared by stimulating an immune cell with a variant of encephalomyocarditis virus, EMC-DV, isolating the immune cell and fusing the immune cell with a tumor cell, and a method of preparing such a hybridoma.

In a further aspect of the present invention, there is provided a method of preparing a VSF protein, comprising culturing a hybridoma prepared as described above, and isolating a VSF protein from the culture fluid of the hybridoma.

In a still further aspect of the present invention, there is provided a method of preparing a VSF protein, comprising injecting a hybridoma prepared as described above into an animal, and isolating a VSF protein from an ascitic fluid obtained from the animal.

The virus, used to obtain stimulated immune cells, is administered into a host by intraperitoneal, intravenous, intramuscular, intraocular or subcutaneous injection, after being properly diluted in a suitable solvent, for example, a physiological saline solution, to prevent induction of physiological disorder and apoptosis in the host. The virus is administered into the host at an amount suitable for inducing the immune response in the host. The preferred dosage of the virus is from $10^3$ to $10^9$ pfu per animal. Administration frequency is typically 2 to 4 at intervals of 1 to 2 weeks. For example, in case of administering the virus four times, the first to third administrations are performed by intraperitoneal injection, and the final administration is by intravenous injection.

3 to 4 days after the final administration, the animal host infected with a virus is anatomized, and then splenocytes are isolated from the excised spleen and used as immune cells. The tumor cells fused with the immune cells include myeloma cells, including mouse-derived cells which are exemplified by p3/x63-Ag8, p3-U1, NS-1, MPC-11, SP-2/0, F0, P3x63 Ag8, V653 and S194, and rat-derived cells such as R-210.

The immune cells infected with a variant of encephalomyocarditis virus, EMC-DV, may be fused with tumor cells by the conventional method, and, from the resulting hybridoma cells, a hybridoma having the highest virus inhibitory effect is selected. Such a hybridoma may be prepared by the conventional immunochemical technique, in which mice and rats may be used.

For example, fusion of immune cells with tumor cells may be achieved by the conventionally known method, which is exemplified by the Koehler & Milstein's method (Koehler et al., Nature 256, 495-497, 1975) that is generally used, and electrofusion using electric pulse. Lymphocytes and a myeloma cell line are mixed at a ratio commonly used in the art, subjected to cell fusion using a FCS-free culture medium containing polyethyleneglycol, which is generally used in the art, and cultured in FCS-containing HAT selection medium to select fused cells (hybridoma cells). In connection with this, the present invention provides a hybridoma producing a VSF protein. The hybridoma of the present invention was deposited with an international depository authority, KCLRF (Korean Cell Line Research Foundation) on Dec. 21, 2001 under the provisions of the Budapest Treaty and has been assigned accession number KCLRF-BP-00052.

The hybridoma can be subcultured by the conventional culturing method, and cryo-preserved according to intended use. VSF protein may be recovered by collecting the culture fluids after culturing the hybridoma by the conventional method, or by injecting the hybridoma into a mammal and then obtaining ascitic fluids from the abdominal cavity of the mammal. VSF protein contained in culture fluids or ascitic fluids may be purified by the conventional method, including salting out, ion exchange and gel filtration chromatography, and affinity column chromatography. Preferably, the VSF protein may be purified by chromatography using a Blue Sepharose column or hydroxyapatite resin column, affinity chromatography using a Protein A agarose column, FPLC, or sucrose gradient centrifugation.

In detail, the VSF protein may be isolated by Blue Sepharose column chromatography, as follows.

The culture fluid of the hybridoma of the present invention or the supernatant of the ascitic fluid is passed through a Blue Sepharose column (Blue Sepharose CL-6B resin column) at a flow rate of 0.1-1.0 ml/min.

Proteins not bound to the column are eliminated by washing the column with sodium phosphate buffer (pH 7.0-7.5) containing 10-60 mM NaCl. Then, sodium phosphate buffer (pH 7.0-7.5) containing 100-300 mM NaCl is added to the column to elute VSF protein, thereby generating active fractions containing VSF protein. Preferably, the culture fluid of the hybridoma or the supernatant of the ascitic fluid is passed through a Blue Sepharose column sufficiently equilibrated with 20 mM sodium phosphate buffer (pH 7.2) at a flow rate of 0.5 ml/min. To eliminate proteins not bound to the column, the column is sufficiently washed with 20 mM sodium phosphate buffer (pH 7.2) containing 50 mM NaCl, where the washing continues until absorbance at 280 nm of the flow through washing buffer falls to a background level.

VSF protein bound to the column is eluted by adding 50 mM sodium phosphate buffer (pH 7.2) containing 200 mM NaCl to the column, thereby giving active fractions. The active fractions are desalted and concentrated using a concentrator.

In addition, the VSF protein according to the present invention may be isolated by chromatography using a Protein A agarose column, as follows. The culture fluid of the hybridoma of the present invention or the supernatant of the ascitic fluid is passed through a Protein A agarose column at a flow rate of 0.1-1.0 ml/min. Proteins not bound to the column are eliminated by washing the column with Tris buffer. Then, acetic acid buffer (pH 4.0-5.0) is added to the column to elute VSF protein, thereby generating active fractions containing the VSF protein The eluted protein is neutralized with 0.1-1.0 M sodium phosphate buffer. Preferably, the culture fluid of the hybridoma or the supernatant of the ascitic fluid is passed through a Protein A agarose column at a flow rate of 0.5 ml/min. To eliminate proteins not bound to the column, the column is sufficiently washed with 0.1 M Tris buffer, where the washing continues until absorbance at 280 nm of the flow through washing buffer falls to a background level. VSF protein bound to the column is eluted by adding acetic acid buffer (pH 4.3) to the column, thereby giving active fractions. The eluted protein is neutralized with 0.5 M sodium phosphate buffer (pH 7.7).

In addition, the VSF protein according to the present invention may be isolated by chromatography using a hydroxyapatite resin column, as follows. The culture fluid of the hybridoma of the present invention or the supernatant of the ascitic fluid is passed through a column filled with hydroxyapatite resin at a flow rate of 0.5-1.5 ml/min. Proteins not bound to the column are eliminated by washing the column with a phosphate-buffered solution. Then, 50-150 mM potassium phosphate buffer (pH 7.0-7.5) is added to the column to elute VSF protein, thereby generating active fractions containing the VSF protein. The collected active fractions are desalted and concentrated using a concentrator. Preferably, a column filled with 15 ml of hydroxyapatite resin is equilibrated with 2 mM phosphate buffer (pH 7.2) containing 1 mM 2-mercaptoethanol and 0.5 mM EDT. A sample according to the present invention flows through the column, and then the column is sufficiently washed with the equilibrating buffer. VSF protein bound to the column is eluted by adding column buffer containing 100 mM potassium phosphate (pH 7.2) to the column, thereby giving active fractions. The collected active fractions are desalted and concentrated until a final concentration of potassium phosphate (pH 7.2) is 2 mM, using a concentrator.

The present invention provides a pharmaceutical composition for prevention and treatment of viral infections in an animal, comprising a therapeutically or preventively effective amount of a VSF protein and a pharmaceutically acceptable carrier, and a method of preventing or treating viral infections, comprising administration of such a pharmaceutical composition.

The therapeutically or preventively effective amount of the VSF protein may be properly determined according to administration subjects, and subjects' age and pathogenic states, and difference between subjects. For example, adult dosage may be about 5 μg-1 mg/kg body weight. In case of oral administration, the pharmaceutically acceptable carrier may include binders, lubricants, disintegrators, excipients, solubilizers, dispersing agents, stabilizers, suspending agents, coloring agents and perfumes. In case of injection preparations, the pharmaceutically acceptable carrier may include buffering agents, preserving agents, analgesics, solubilizers, isotonic agents and stabilizes. In case of preparations for local administration, the pharmaceutically acceptable carrier may include bases, excipients, lubricants and preserving agents. The pharmaceutical composition may be formulated into a variety of dosage forms in combination with the aforementioned pharmaceutically acceptable carrier. For example, for oral administration, the pharmaceutical composition may be formulated into tablets, troches, capsules, elixirs, suspensions, syrups or wafers. For injection preparations, the pharmaceutical composition may be formulated into a unit dosage form, such as a multidose container or an ampule as a single-dose dosage form.

The antiviral pharmaceutical composition according to the present invention may be administered orally, or parenterally, i.e., by intravenous, subcutaneous, intranasal or intraperitoneal administration, to humans or animals. The oral administration includes sublingual application. The parenteral administration includes injection methods such as subcutaneous, intramuscular or intravenous injection, and drip injection.

In addition, the pharmaceutical composition according to the present invention may be formulated into other forms according to the conventional method.

The present invention will be explained in more detail with reference to the following an example in conjunction with the accompanying drawings. However, the following example is provided only to illustrate the present invention, and the present invention is not limited to the example.

EXAMPLE 1

Preparation of Hybridomas Producing VSF Protein

The EMCV variant EMC-DV, was intraperitoneally injected into five 8 week-old BALB/c mice (female) at an amount off $5 \times 10^4$ pfu (plaque forming unit)/mouse. After 7 days, $10^7$ pfu of EMC-DV was intravenously injected. After 4 days, mice were sacrificed to excise spleens. The splenocytes obtained from the excised spleens were fused with myeloma cells (V653) using polyethylene glycol.

The resulting fused cell clones were subjected to a virus inhibition test (VIT) to screen cell lines having high antiviral activity. VIT was performed using DMEM (Gibco) containing 2% FCS. 50 μl of culture fluid serially diluted over four times was aliquotted into each well of a 96-well plate. $5 \times 10^4$ L cells (murine fibroblasts) were put into each well of the plate. After incubation for 1 hr, 100 pfu of EMCV was added to each well, to make a total volume of 200 μl, followed by incubation at 37° C. for 48 hrs. After incubation, the culture medium was removed, and then 150 μl of 10% formaldehyde was added to each well, and the plate was incubated at room temperature for 10 min to allow fixation of L cells. 50 μl of 1% crystal violet solution was added to each well, followed by incubation at room temperature for 10 min to allow staining. Thereafter, the added solutions were removed, and the plate was lightly washed with water to eliminate background stain. Cellular viability was evaluated by analyzing stained degree of the cells.

When viral proliferation is suppressed, all cells survive, forming a uniform layer, and are stained with crystal violet, giving a uniformly stained layer. In contrast, when cells are lyzed by viral infection, the cells are detached, thereby yielding rarely stained layer when being stained.

In addition, inhibitory effect of the VSF protein against viruses was analyzed by investigating cellular viability using MTS ([3-(4,5-dimethylthiazol-2-yl)-5-(3-carboxymethoxyphenyl)-2-(4-sulfophenyl)-2H-tetrazolium], inner salt Promega), which is used for measurement of metabolic rates of cells. According to the protocol recommended by the manufacturing company, appropriate cells were plated into a 96-well plate at a density of $10^4$ cells, and treated with the culture fluid containing VSF protein of various concentrations, as well as with a virus. After incubation for a predetermined time according to life cycle of the virus the cells were treated with 20 μl of a MTS solution, and then absorbance at 490 nm was measured.

The higher cellular viability is, the stronger absorbance at 490 nm is. Cellular viability was calculated from the measured absorbance values.

As a rest a hybridoma cell line 4D1B having excellent antiviral activity was obtained, and deposited in an international depository authority, KCLRF (Korean Cell Line Research Foundation) on Dec. 21, 2001 under the provisions of the Budapest Treaty and has been assigned accession number KCLRF-BP-00052.

EXAMPLE 2

Production of Ascitic Fluids

The hybridoma 4D1B (accession number KCLRF-BP-00052) prepared in Example 1 was inoculated in DMEM containing 2% FCS, and incubated at 37° C. under 5% $CO_2$. $1 \times 10^7$-$2 \times 10^7$ cells of the cultured hybridma were intraperitoneally injected into mice. After about 2 weeks, ascitic fluids were collected from the swelled abdominal cavities of mice, and centrifuged at 1500×g. The resulting supernatants were aliquotted to a small volume, as described above, and stored at −70° C. until use.

EXAMPLE 3

Sensitivity of VSF Protein to Proteinase

The VSF protein according to the present invention was evaluated for sensitivity to proteinase. In this test, proteinase K was used, which has specific activity of 30 units/mg. The hybridoma 4D1B (accession number KCLRF-BP-00052) prepared in Example 1 was inoculated in SFM (serum-free media, Gibco), and incubated at 37° C. under 5% $CO_2$. Proteinase K was added to the culture fluid at an amount of 1, 2 and 4 mg/ml, followed by incubation at 37° C. for 1 hr. Separately, trypsin, having specific activity of 10,000 BAEE units/mg protein, was added to the culture fluid at an amount of 1 mg/ml, followed by incubation for 3 hrs. Antiviral activity of VSF protein contained in the culture fluid was analyzed by VIT and MTS assay as described in Example 1.

As a result, even when treated with a minimum amount of proteinase K, VSF protein lost its antiviral activity. In contrast, in case of being treated with trypsin, VSF protein was found to retain weak antiviral activity. These results indicate that all or some subunits of the VSF protein are very sensitive to proteinase K.

EXAMPLE 4

Evaluation of the Hybridoma for Expression of Cytokines by RT-PCR

The hybridoma 4D1B (accession number KCLRF-BP-00052) secreting VSF protein, prepared in Example 1, was evaluated for expression of specific cytokines by RT-PCR. RT-PCR was carried out to the hybridoma 4D1B and the negative controls which were the splenocytes from mice used in preparing fused cells in Example 1 and a hybridoma not having antiviral activity, as follows.

Total RNA was isolated from the above cells using Trizol reagent (Gibco-BRL). Chemical reagents used in RT-PCR were purchased from Promega. To a sterilized microtube, 5 μg of total RNA, 8 μl of 5× reverse transcriptase buffer, 8 μl of 10 mM dNTP, 100 pmole of oligo(dT), 40 units of RNasin, and 200 units of MMLV reverse transcriptase were added, and total volume of the m was adjusted to 40 μl using DEPC (diethyl pyrocarbonate)-treated water. Then, the mixture was incubated at 42° C. for 1 hr, and then at 95° C. for 3 min, thus yielding a cDNA sample.

The cDNA sample was subjected to PCR using a primer set capable of amplifying a specific cytokine. The primer sets (synthesized by Bioneer, Korea) are listed in Table 1, below, and can amplify cytokines including IL, IFN, TNF, TGF, CSF and chemokines. To a premix tube, 1 μl of a cDNA sample, 10 pmole of forward primer and 10 pmole of reverse primer were added, and total volume of the mixture was adjusted to 20 μl using sterilized water. PCR was carried out under conditions of denaturation at 94° C. for 3 min, and 45 cycles of denaturation at 94° C. for 1 min, annealing at 60° C. for 1 min and extension at 72° C. for 1 min, followed by final extension at 72° C. for 3 min.

TABLE 1

Primers for RT-PCR

| Primer name | Sequence | SEQ ID NO | Primer name | Sequence | SEQ ID NO |
| --- | --- | --- | --- | --- | --- |
| IL-1aF | cagcaccttacacctaccagag | 5 | IL-1aR | ctggaagtctgtcatagagg | 6 |
| IL-1bF | gcagctatggcaactgttcc | 7 | IL-1bR | ggaagacacagattccatggtg | 8 |
| IL-2F | atgtacagcatgcagctcgc | 9 | IL-2R | gagggcttgttgagatgatgc | 10 |
| IL-3F | atggttcttgccagctctaccac | 11 | IL-3R | ttaacattccacggttccacgg | 12 |
| IL-4F | atgggtctcaaccccagctag | 13 | IL-4R | gatgctcttaggctttccagg | 14 |
| IL-5F | cagagtcatgagaaggatgc | 15 | IL-5R | tcagccttccattgcccactctg | 16 |
| IL-6F | gaagttcctctctgcaagag | 17 | IL-6R | ctaggtttgccgagtagatctc | 18 |
| IL-7F | cgcagaccatgttccatgtttc | 19 | IL-7R | ggaggttgttactacatgtcctg | 20 |
| IL-9F | ggtgacatacatccttgcctc | 21 | IL-9R | tcatggtcggcttttctgcc | 22 |
| IL-10F | atgcctggctcagcactgctatg | 23 | IL-10R | catggccttgtagacaccttg | 24 |
| IL-11F | atgaactgtgtttgtcgcctgg | 25 | IL-11R | tcccgagtcacagtcgagtc | 26 |
| IL-12aF | atgtgtcaatcacgctacctcctc | 27 | IL-12aR | tcaggcggagctcagatagc | 28 |
| IL-12bF | atgtgtcctcagaagctaacc | 29 | IL-12bR | atcctaggatcggaccctgc | 30 |
| IL-13F | ttcatggcgctctgggtgac | 31 | IL-13R | tcattagaaggggccgtggc | 32 |
| IL-15F | gaggaatacatccatctcgtgc | 33 | IL-15R | cagtcaggacgtgttgatgaac | 34 |
| IL-16F | cacggttcacagagtgtttcc | 35 | IL-16R | ctatgagtctgcagaagctg | 36 |
| IL-17F | atgagtccagggagagcttc | 37 | IL-17R | ttaggctgcctggcggacaatc | 38 |
| IL-18F | atggctgccatgtcagaagac | 39 | IL-18R | gcatcatcttccttttggcaagc | 40 |
| G-CSFF | atggctcaactttctgcccag | 41 | G-CSFR | ctaggccaagtggtgcagagc | 42 |
| GM-CSFF | tgaggaggatgtggctgcag | 43 | GM-CSFR | gcttcctcattttggactgg | 44 |
| TNF-αF | atgagcacagaaagcatgatccg | 45 | TNF-αR | cttcacagagcaatgactcc | 46 |
| TNF-βF | atgacactgctcggccgtct | 47 | TNF-βR | gaatctacagtgcaaaggctcc | 48 |
| IFN-αF | cataatggctaggcccttgtc | 49 | IFN-αR | tcactccttctcctcactcag | 50 |
| IFN-βF | atgaacaacaggtggatcctcc | 51 | IFN-βR | ctgacaggtcttcagttttgg | 52 |
| IFN-γF | atgaacgctacacactgcatc | 53 | IFN-γR | tcagcagcgactccttttcc | 54 |
| TGF-βF | gcgctcactgctcttgtgac | 55 | TGF-βR | ttcagctgcacttgcaggag | 56 |
| RANTESF | atgaagatctctgcagctgcc | 57 | RANTESF | cctctatcctagctcatctcc | 58 |
| MIP-1αF | atgaaggtctccaccactgc | 59 | MIF-1αR | ctcaggcattcagttccagg | 60 |
| MIP-1βF | atgaagctctgcgtgtctgc | 61 | MIF-1βR | ctggagctgctcagttcaac | 62 |
| MIP-1γF | atgaagccttttcatactgccc | 63 | MIP-1γR | gttattgtttgtaggtccgtgg | 64 |
| MCP-1F | atgcaggtccctgtcatgcttc | 65 | MCP-1R | ctagttcactgtcacactggtc | 66 |

TABLE 1-continued

Primers for RT-PCR

| Primer name | Sequence | SEQ ID NO | Primer name | Sequence | SEQ ID NO |
|---|---|---|---|---|---|
| MCP-3F | atgaggatctctgccacgcttc | 67 | MCP-3R | cttcaaggctttggagttgggg | 68 |
| IP-10F | atgaacccaagtgctgccgt | 69 | IF-10R | cagttaaggagccctttttagacc | 70 |
| LymphotactinF | atgagacttctcctcctgac | 71 | LyphotactinR | ctgttacccagtcagggtta | 72 |
| GapdhF | tgatgggtgtgaaccacgag | 73 | GapdR | cttactccttggaggccatg | 74 |

As a result it was found that there is no expression of specific cytokines in the hybridoma secreting the VSF protein of the present invention, and this result was reproduced in repeated experiments (Table 2, O: expression of cytokine). This result indicates that the VSF protein of the present invention does not comprise any conventionally known cytokine, and thus may be a new protein.

TABLE 2

RT-PCR result for cytokine expression

| No. | Cytokine | bp | Splenocytes | Control hybridoma | Hybridoma of the present invention |
|---|---|---|---|---|---|
| 1 | IL-1alpha | 461 | O | | |
| 2 | IL-1beta | 813 | O | | |
| 3 | IL-2 | 505 | | | |
| 4 | IL-3 | 501 | | | |
| 5 | IL-4 | 402 | O | | |
| 6 | IL-5 | 409 | | | |
| 7 | IL-6 | 634 | O | | |
| 8 | IL-7 | 497 | O | | |
| 9 | IL-9 | 430 | O | | |
| 10 | IL-10 | 474 | O | O | O |
| 11 | Il-11 | 607 | | | |
| 12 | IL-12a | 648 | | | |
| 13 | IL-12b | 1011 | | | |
| 14 | IL-13 | 402 | | O | O |
| 15 | IL-15 | 469 | O | O | O |
| 16 | IL-16 | 574 | O | O | O |
| 17 | IL-17 | 477 | | | |
| 18 | IL-18 | 497 | O | O | O |
| 19 | G-CSF | 627 | | | |
| 20 | GM-CSF | 440 | | | |
| 21 | TNF-α | 710 | O | | |
| 22 | TFN-β | 613 | O | | |

TABLE 2-continued

RT-PCR result for cytokine expression

| No. | Cytokine | bp | Splenocytes | Control hybridoma | Hybridoma of the present invention |
|---|---|---|---|---|---|
| 23 | IFN-α | 577 | | | |
| 24 | IFN-β | 560 | | | |
| 25 | IFN-γ | 468 | O | | |
| 26 | TGF-β | 516 | O | O | O |
| 27 | RANTES | 284 | O | O | |
| 28 | MIP-1α | 280 | O | | |
| 29 | MIP-1β | 289 | O | | |
| 30 | MIP-1γ | 370 | O | | |
| 31 | MCP-1 | 447 | O | | |
| 32 | MCP-3 | 296 | | O | |
| 33 | IP-10 | 300 | O | O | |
| 34 | Lymphotactin | 348 | O | | |
| 35 | Gapdh | 615 | O | O | O |

EXAMPLE 5

Purification of VSF Protein by Blue Sepharose Column Chromatography

The hybridoma 4D1B (accession number KCLRF-BP-00052) was cultured in 20% FCS-containing DMEM, and then SFM (serum-free medium) or PFM (protein-free medium). The medium was exchanged with a fresh medium at intervals of 2 days. The culture fluids were collected, and centrifuged at 1500×g to remove cell debris.

The supernatant was passed through a Blue Sepharose column at a flow rate of 0.5 ml/min. To eliminate proteins not bound to the column, the column was sufficiently washed with 20 mM sodium phosphate buffer (pH 7.2) containing 50 mm NaCl. Then, 50 mM sodium phosphate buffer (pH 7.2)

containing 200 mM NaCl was added to the column, and active fractions containing VSF protein were collected.

EXAMPLE 6

Purification of VSF Protein by Protein a Affinity Column Chromatography

The hybridoma 4D1B (accession number KCLRF-BP-00052) was cultured in 20% FCS-containing DMEM, and then SFM (serum-free medium) or PFM protein-free medium). The medium was exchanged with a fresh medium at intervals of 2 days. The culture fluids were collected, and centrifuged at 1500×g to remove cell debris.

An affinity column was eared using Protein A agarose bead (Sigma, Cat. #P-2545). The supernatant was passed through the affinity column at a flow rate of 0.5 ml/min. Active fractions containing VSF protein were collected by adding acetic acid buffer (pH 4.3) to the column.

EXAMPLE 7

Purification of VSF Protein by Hydroxyapatite Column Chromatography

The hybridoma 4D1B (accession number KCLRF-BP-00052) was cultured in 20% FCS-containing DMEM, and then SFM (serum-free medium) or PFM (protein-free medium). The medium was exchanged with a fresh medium at intervals of 2 days. The culture fluids were collected, and centrifuged at 1500×g to remove cell debris.

A column filled with hydroxyapatite resin was equilibrated with 2 mM phosphate buffer (pH 7.2) containing 1 mM 2-mercaptoethanol and 0.5 mM EDTA. The supernatant was passed through the column at a flow rate of 0.5 ml/min. After sufficiently washing the column with the aforementioned buffer, active fractions containing VSF protein were collected by adding 100 mM potassium phosphate (pH 7.2) to the column.

EXAMPLE 8

Analysis of Active Fractions Containing VSF Protein by SDS-PAGE

The active fractions containing VSF protein, prepared in Examples 5 to 7, was analyzed by SDS-PAGE and Western blotting, in which proteins were detected by staining with Coommassie Blue and immunostaining using AP-conjugated anti-mouse IgG antibody. 5 μl of each active fraction was mixed with 2×SDS sample buffer, boiled for 5 min, cooled, and loaded onto a 12% SDS-polyacrylamide gel.

After electrophoresis, proteins separated on the gel were identified by staining with Coommassie Blue dye, and then destaining using an acetic acid-methanol mixture to remove background staining. Separately, to detect proteins by Western blotting, each active fraction was separated on a SDS-polyacrylamide gel according to the same method as described above, and transferred onto a nitrocellulose membrane. The membrane was washed with distilled water and dried. After being blocked for 1 hr 30 min in 5% skim milk dissolved in Blotto (TBS (tris-buffered saline)), and washed with TBS and dried, the membrane was reacted with alkaline phosphatase (AP)-conjugated goat anti-mouse IgG for 1 hr. The membrane was washed three times with TBS containing Tween 20 at intervals of 10 min, and then with AP buffer (100 mM Tris buffer containing 5 mM $MgCl_2$, pH 9.5) for 10 min. Thereafter, the membrane was developed using 10 ml AP buffer supplemented with 66 μl of a NBT stock solution prepared by dissolving NBT (nitroblue tetrazolium) at a concentration of 50 mg/ml in 70% DMF (dimethylformamide), and 30 μl of a BCIP stock solution prepared by dissolving BCIP (bromochloroindolyl phosphate) at a concentration of 50 mg/ml in 100% DMF. When the development reached a suitable strength, the blot was washed with distilled water several times to stop the color reaction.

As shown in FIG. 1, major bands of the active fractions obtained using three different columns were found to be almost identical. 3 major bands were present at identical positions in three kinds of active fractions, and one band among them was identified to be a doublet upon magnifying the gel image. One band (about 55 kDa), two bands (about 30 kDa) and one band (about 25 kDa) were designated 'H', 'L1' and 'L2', and 'L3', respectively. Herein, in case of the active fractions obtained using a Protein A agarose resin, an antibody-like molecule was found to be isolated. It is believed that the molecule is not just an antibody to a specific molecule, but a member of the immunoglobulin superfamily, or that a part of an antibody is required for action of the VSF protein.

EXAMPLE 9

Determination of Molecular Weight of VSF Protein Using Centricon™

Molecular weight of the VSF protein according to the present invention was determined using Centricon membranes (Amicon) with 30, 50, 100 and 500 kDa pores. The active fractions prepared in Examples 5 to 7 were loaded onto a Centricon membrane with 30 kDa pore, followed by centrifugation at 5000×g. Fluids passed through the Centricon membrane with 30 kDa pore were stored, and the remaining fraction solutions were subjected to a Centricon membrane with a larger size pore, where the Centricon membranes with 50, 100 and 500 kDa pores were used sequentially. Fluids passed through each Centricon membrane were analyzed for antiviral activity according to the same method as in Example 1, as well as for protein distribution by SDS-PAGE.

As shown in Table 3, below, antiviral activity was found mainly in the fractions containing over 500 kDa proteins and 100 to 500 kDa proteins, while weak antiviral activity was found in the fraction containing less than 100 kDa proteins. These results were identical to the SDS-PAGE its as shown in FIG. 2. It was shown that major protein did not pass through Centricon of 500 kDa pore with a relatively small portion being present in 100 to 500 kDa pore. These results indicates that the VSF protein is actually present at a large complex form with a molecular weight of at least over 100 kDa, which is a minimum unit capable of displaying antiviral activity. The conventional CAF was known to have a molecular weight of less than 30 kDa, when isolated according to the method as described above. Therefore, it is believed that the VSF protein of the present invention is completely different from CAF. Moreover, with consideration of the fact that most of the conventionally known antiviral cytokines have a molecular weight of less than 100 kDa, it appears that the VSF protein does not comprise any of the conventionally known antiviral cytokines.

TABLE 3

Assay result for antiviral activity of fluids passed through Centricon ™

| Pore size of Centricon ™ | VIT# | Total protein amount (mg/ml) |
|---|---|---|
| >500 kDa | 1,024 | 0.32 |
| 100–500 kDa | 256 | 0.2 |
| 50–100 kDa | 1 | 0.14 |

VIT#: Virus Inhibition Test: maximum dilution times capable of detecting antiviral activity

EXAMPLE 10

Evaluation for Antiviral Activity of VSF Protein Against EMCV and Mengo Virus

The culture fluid of the hybridoma 4D1B (accession number KCLRF-BP-00052), and ascitic fluids prepared in Example 2, were evaluated for antiviral activity against EMCV and Mengo virus according to the same method as in Example 1.

Figure 3:
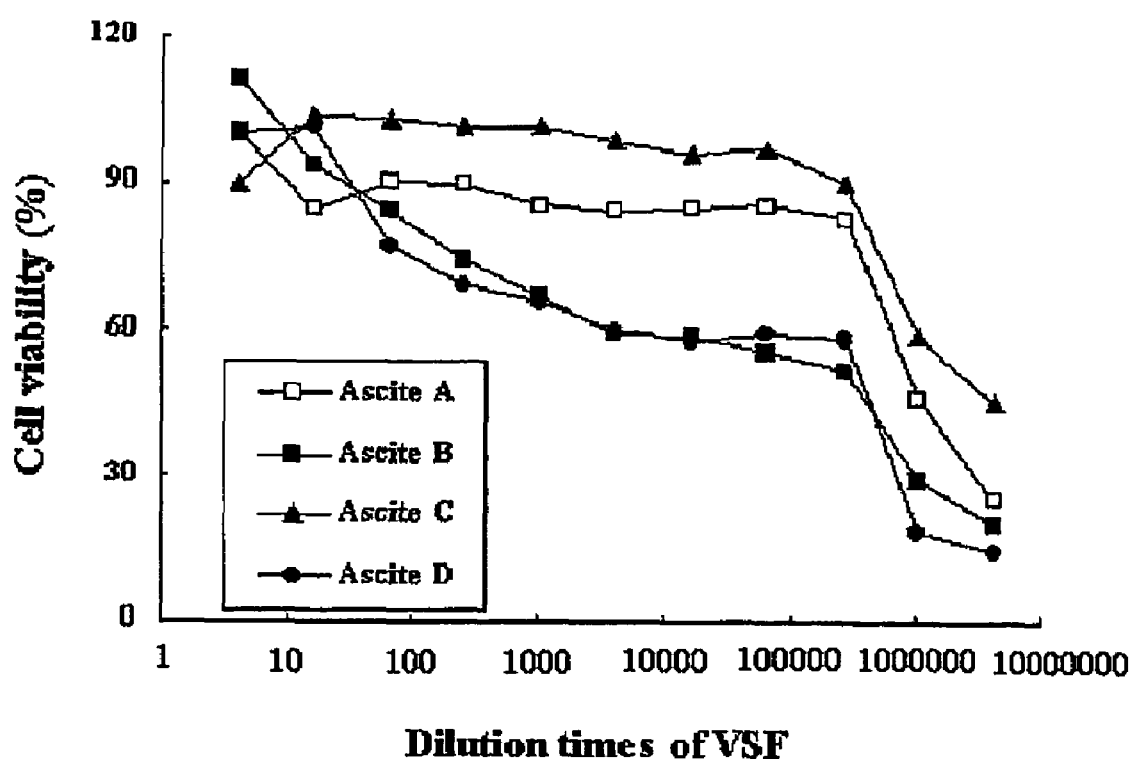
FIG. 3 is a graph showing antiviral activity of ascitic fluids, obtained from mice intraperitoneally administered with a hybridoma according to the present invention, against Encephalomyocarditis virus (EMCV) and Mengo virus, where antiviral activity is analyzed by MTS assay.

As shown in Table 4, below, the VSF protein was found to strongly suppress proliferation of EMCV and Mengo virus. Even when diluted over 2048 times, VSF protein contained in the culture fluid retained antiviral activity, while VSF protein contained in the ascitic fluids had antiviral activity even when diluted one million times. Also, these results were confirmed by MTS assay (FIG. 3).

The conventionally known CAF was reported to retain antiviral activity only up to a 10-fold dilution (Walker C M et al., Immunology, 66, 628-630 (1989), Carl E M et al., PNAS, 92, 2308-2312 (1995)), whereas the VSF protein of the present invention was demonstrated to have very strong antiviral activity. In addition, the VSF protein showed no cytotoxic activity even when cells were treated with the highest concentration of the VSF protein, indicating that antiviral activity of the VSF protein is not based on apoptosis, and the VSF protein has very low cytotoxic activity.

TABLE 4

Inhibitory effect of VSF protein on proliferation of EMCV and Mengo virus

| | Culture fluid | Ascitic fluid A | Ascitic fluid B | Ascitic fluid C | Ascitic fluid D |
|---|---|---|---|---|---|
| VIT# | 2,048 | 1,048,576 | 1,048,576 | 4,194,304 | 1,048,576 |

VIT#: Virus Inhibition Test: maximum dilution times capable of detecting antiviral activity

EXAMPLE 11

Evaluation for Antiviral Activity of VSF Protein Against Influenza Virus

The culture fluid of the hybridoma 4D1B (accession number KCLRF-BP-00052), and ascitic fluids prepared in Example 2, were evaluated for antiviral activity against influenza virus, as follows. After incubation for 8 days, embryonated chicken eggs were inoculated with influenza virus. First, after selecting areas not having blood vessels of the eggs as inoculation sites, the surface of the shell on the inoculation sites was disinfected. After punching the shell containing the shell membrane to make a small hole, influenza virus was inoculated into the allantoic cavity through the hole using a microinjector. Then, the hole was sealed with drops of melted wax. Herein, 1 HAU (hemagglutination unit) of influenza virus was inoculated, and 10-200 μl of the culture fluid of the hybridoma or the ascitic fluid was inoculated After incubation for 2 days at 34° C., some of the inoculated eggs were placed at 4° C. overnight, and a part of the shell was broken to collect the allantoic fluid. The remaining eggs were further incubated for 3 more days, and the shell was removed and viability of the embryos was investigated. The collected allantoic fluids were subjected to hemagglutination assay. The allantoic fluids were serially diluted with phosphate-buffered saline several times. An equal volume of a 0.5% suspension of chicken blood cells was added to each of the diluted allantoic fluids, followed by incubation at room temperature for 30 min. When hemagglutination is induced by viruses, a thin layer of agglutinated blood cells is formed on the bottom of a test tube.

Proliferation degree of influenza virus was evaluated by the hemagglutination assay.

Figure 4:
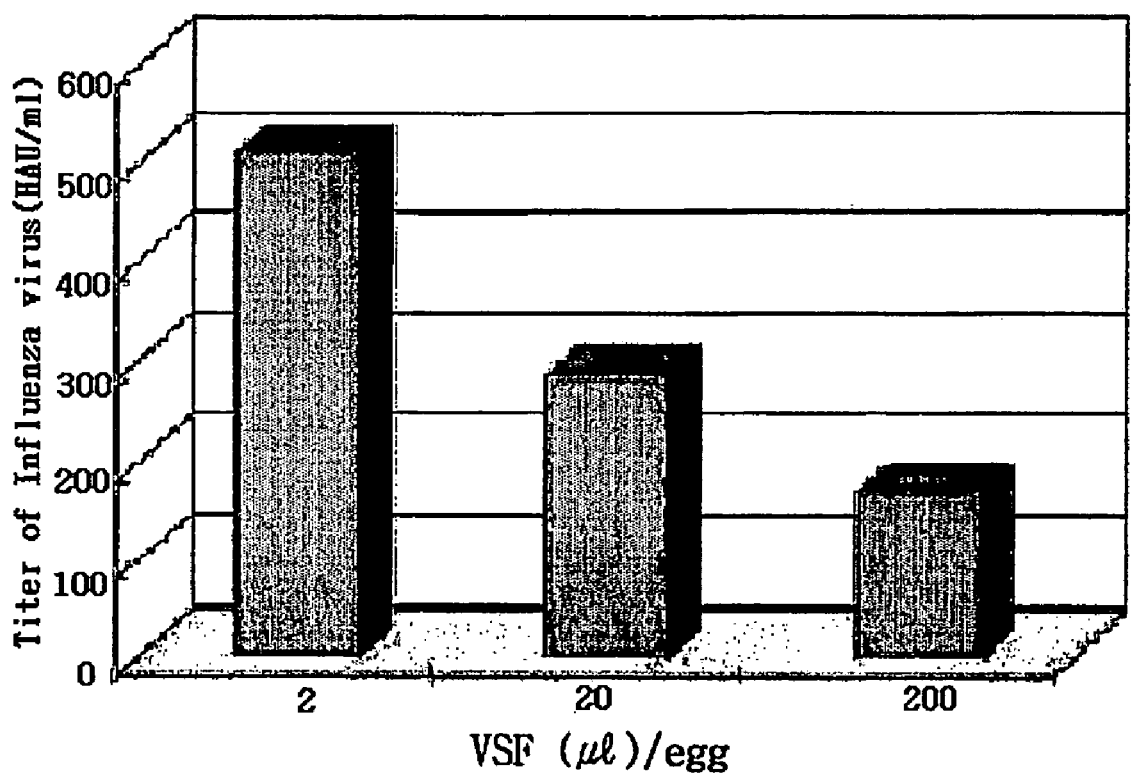
FIG. 4 is a graph showing antiviral activity of culture fluid of a hybridoma according to the present invention, against influenza virus.
Figure 5:
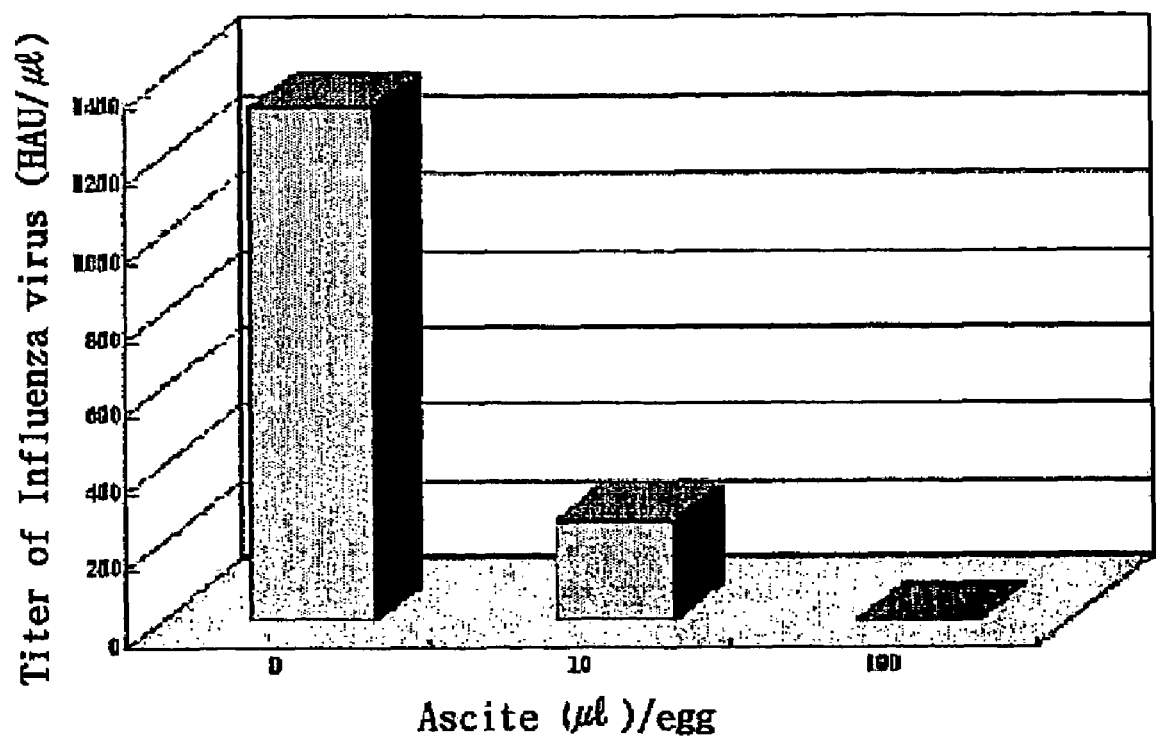
FIG. 5 is a graph showing antiviral activity of ascitic fluids, obtained from mice intraperitoneally administered with a hybridoma according to the present invention, against influenza virus.

As a result, VSF protein contained in both of the culture fluids and ascitic fluids was found to effectively inhibit proliferation of influenza virus, resulting in improvement of viability of the embryos. As shown in FIG. 4, when VSF protein was inoculated at the culture fluid state, the VSF protein was found to inhibit proliferation of influenza virus in a dose-dependant manner. In addition, as shown in FIG. 5, VSF protein contained in the ascitic fluids effectively suppressed proliferation of influenza virus, where the VSF protein was found not to negatively affect growth of the embryonated chicken eggs.

EXAMPLE 12

Evaluation for Antiviral Activity of VSF Protein Against HIV $10^4$ SupT1 cells (human T cell line, Smith S D et al., Cancer Research, 44, 5657-5660, (1984)) were infected with about $10^3$ $TCID_{50}$ of HIV-1 (NL strain). Simultaneously with the infection, the serially diluted ascitic fluid prepared in Example 2 was added to the cells. Then, the cells were cultured in RPMI 1640 medium (Gibco) containing 10% FCS at 37° C. under 5% $CO_2$. Proliferation degree of HIV was evaluated by investigating formation of multinucleated giant cells called syncytia, which are formed 4 to 5 days after infection.

Figure 6:
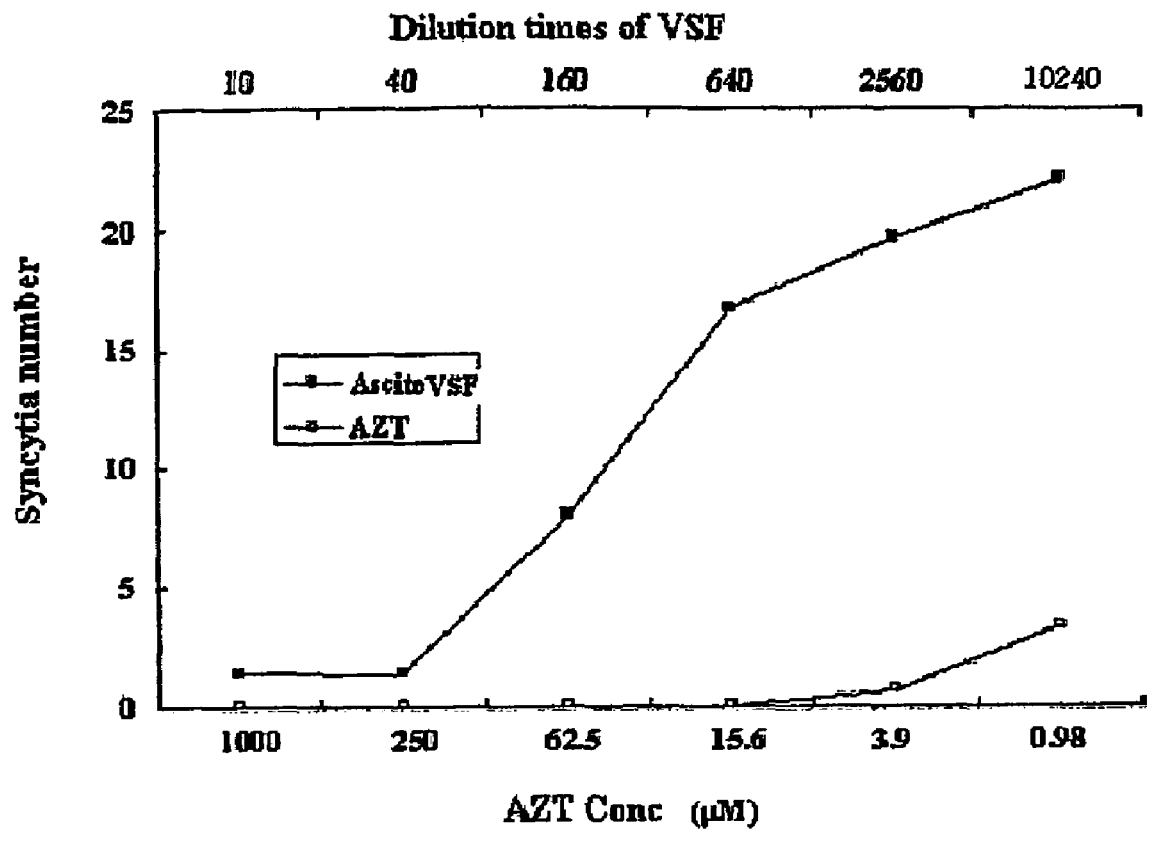

As shown in FIG. 6, when SupT1 cells were treated with the ascitic fluid containing VSF protein, simultaneously with viral infection, VSF protein reduce syncytia formation in a dose-dependant manner.

In addition, the VSF protein contained in the ascitic fluid was found to have no negative effect on proliferation of the control cells.

EXAMPLE 13

Evaluation for Inhibitory Effect of VSF Protein on Induction of Diabetes Mellitus by EMCV When SJL/J mice are infected with EMCV, they develop diabetes mellitus. In this test, it was investigated whether such induction of diabetes mellitus by EMCV is inhibited by the VSF protein. 9 week-old SJL/J mice (male) were divided into five groups, each of which comprised 6 mice according to administration and administration time of VSF protein. Group 1 was administered with only VSF protein, and Group 2 was administered with only EMC-D. Group 3 was administered with VSF protein simultaneously with infection with EMC-D. Group 4 was infected with EMC-D, and, after 4 hrs, administered with VSF protein. Group 5 was infected with EMC-D, and, after 24 hrs, administered with VSF protein. $10^4$ pfu (0.5 ml) of EMC-D was intraperitoneally injected into mice. 0.5 ml of the culture fluid containing VSF protein was injected once into the tail vein of mice. From day 2 after infection with EMC-D, urine was collected from mice of each group every day to perform diagnosis of diabetes mellitus.

Figure 7:
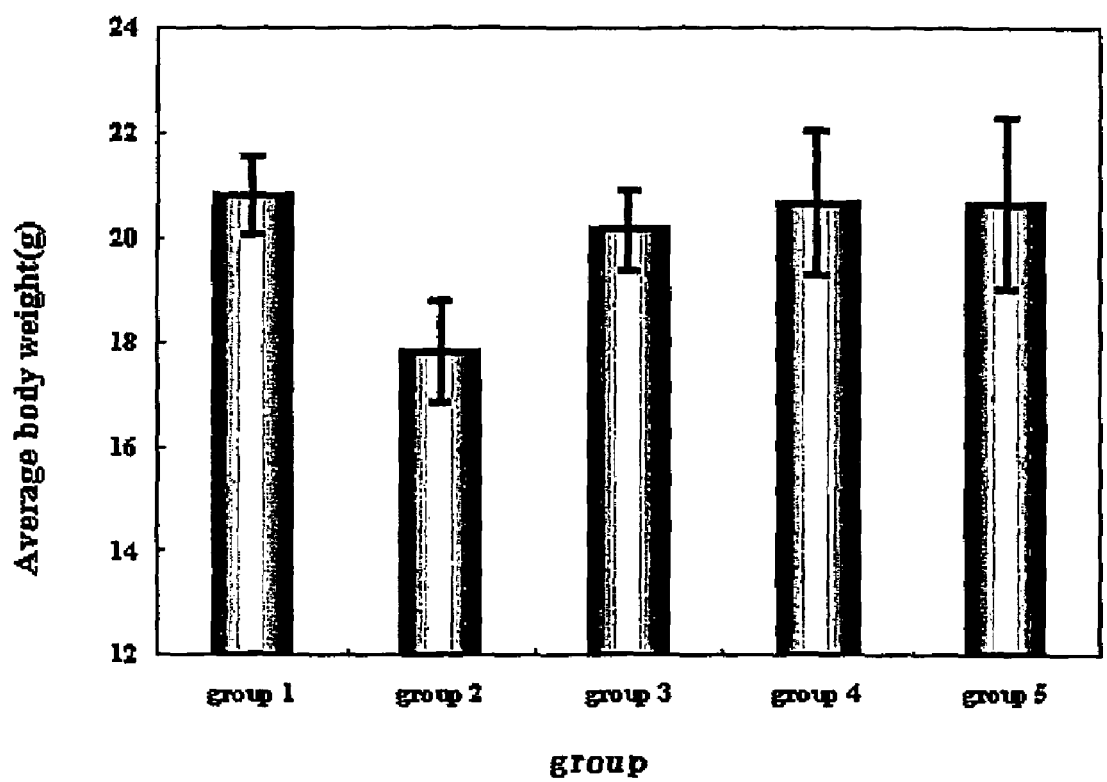
FIG. 7 is a graph showing inhibitory effect of culture fluid of a hybridoma according to the present invention on induction of diabetes mellitus by EMCV, where body weight of mice infected with EMCV (group 2) is compared with that of EMCV-infected mice treated with the culture fluid (groups 3 to 5) 1 week after viral infection.

As shown in Table 5, below, and FIG. 7, no symptom of disease was found in Group 1 administered with only VSF protein, indicating that the VSF protein has no cytotoxic effect or side effects. In case of Group 2 administered with only EMC-D, all 6 mice showed severe diabetic symptoms on day 4 after viral infection, accompanied with reduction of body weight, and, moreover, two of the 6 mice died on day 10. In case of Group 3 administered with VSF protein simultaneously with vial infection, no diabetes mellitus was detected, and mice were in a healthy state. Also, in Group 4 administered with VSF protein 4 hrs after viral infection, no diabetes mellitus was detected, and mice were in a healthy state. In case of Group 5, administered with VSF protein after 24 hrs of viral infection, diabetes mellitus was not developed, and reduction of body weight was not found.

These results demonstrate that the VSF protein has strong antiviral activity in vivo as well as in vitro.

In case of the conventional CAF, its antiviral activity was reported to rapidly decrease when being diluted, thereby not allowing in vivo experiments. Interferon is disadvantageous in terms of having remarkably reduced antiviral activity when being externally injected into the body, in comparison with when being naturally expressed in the body. In contrast in this test, the VSF protein, only 0.5 ml of culture fluid, showed an effect of perfectly inhibiting development of diabetes mellitus by EMCV, and was found not to be cytotoxic. These results indicate that the VSF protein has a potential to be developed to a novel drug.

Furthermore, such a perfect effect of inhibiting development of diabetes mellitus was also found even when the VSF protein was administered to mice 24 hrs before viral infection. This result indicates that the VSF protein is useful for prevention as well as treatment of vial infections.

TABLE 5

Development of diabetes mellitus in mice infected with EMC-D according to administration of VSF protein and its administration time

| Group | Immediately before viral infection | Day 3 after viral infection | Day 4 after viral infection | Day 7 after viral infection |
|---|---|---|---|---|
| 1 | — | — | — | — |
| 2 | — | — | 6/6 | 6/6 |
| 3 | — | — | — | — |
| 4 | — | — | — | — |
| 5 | — | — | — | — |

EXAMPLE 14

Evaluation for Inhibitory Effect of VSF Protein on Proliferation of HCMV

The culture fluid of the hybridoma 4D1B secreting VSF protein according to the present invention was evaluated for antiviral activity against HCMV (Human Cytomegalovirus). According to the same method as in Example 1, HCMV was treated with several dilutions of the culture fluid of the hybridoma 4D1B.

As a result, even when diluted 4 to 16 times, the culture fluid of the hybridoma 4D1B was found to perfectly inhibit proliferation of HCMV. This result s the finding that the VSF protein has antiviral activity against a variety of viruses.

EXAMPLE 15

Determination of Molecular Weight of VSF Protein by FPLC

The hybridoma 4D1B (accession number KCLRF-BP-00052) was cultured in 20% FCS-containing DMEM, and then SFM (serum-free medium) or PFM (protein-free medium). The medium was exchanged with a fresh medium at intervals of 2 days. The culture fluids were collected, and centrifuged at 1500×g to remove cell debris.

The supernatant was subjected to FPLC (Fast Flow Performance Liquid Chromatography) using a column filled with Superdex 200 HR 10/30 resin (Pharmacia Biotech, 17-1088-01). The supernatant was passed through the column at a flow rate of 0.5 ml/min. Active fractions containing VSF protein were collected by adding 0.05 M sodium phosphate buffer (pH 7.0) containing 0.15 M NaCl to the column.

Figure 8:
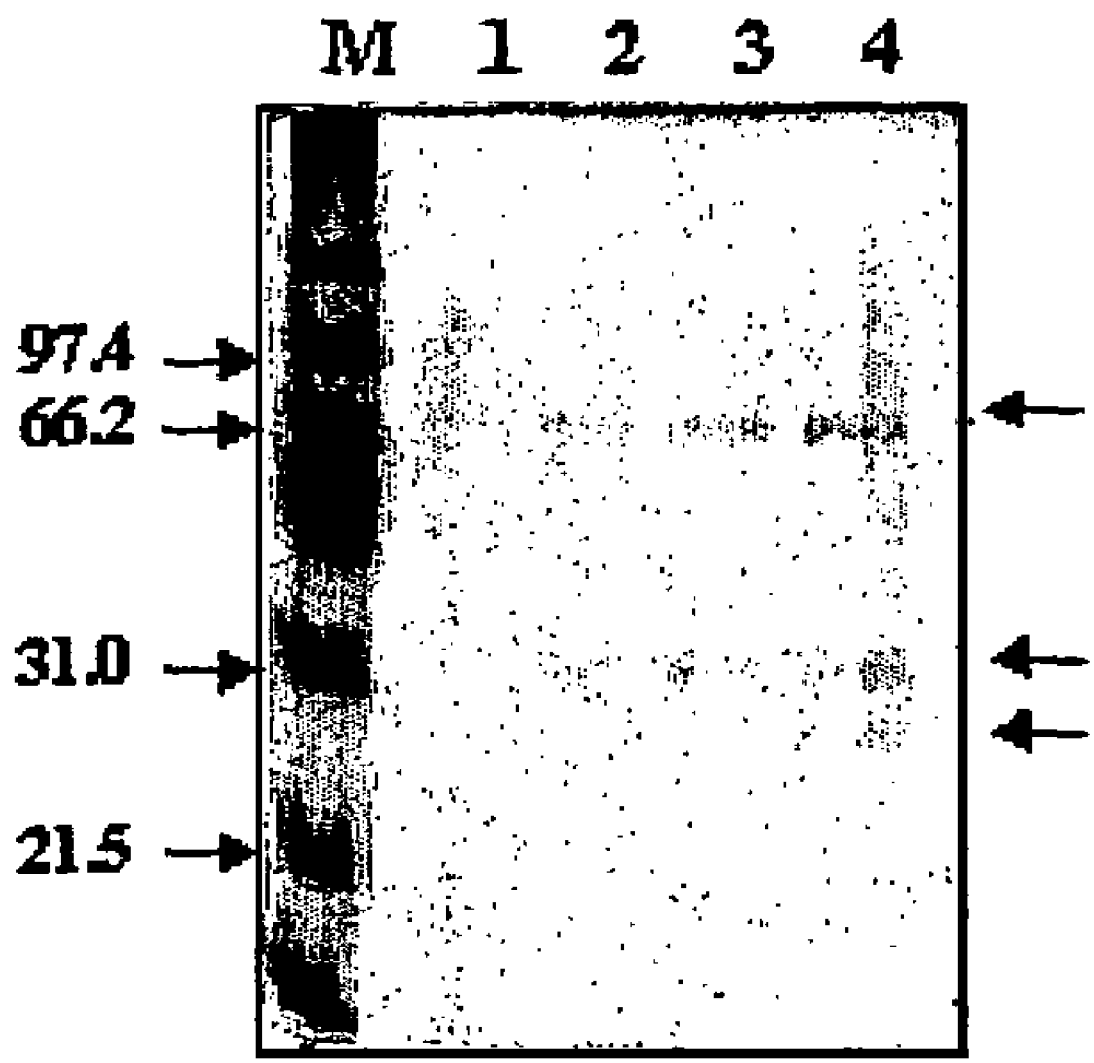
FIG. 8 is a photograph showing a result of SDS-PAGE of a VSF fraction, which is obtained by FPLC in which a VSF protein according to the present invention is identified to have a molecular weight of about 163 kDa (lanes 3 and 4: about 163 kDa fraction having antiviral activity)

As a result of SDS-PAGE, four major bands were, as shown in lanes 3 and 4 of FIG. 8, found in two about 163 kDa fractions. This band pattern was identical to SDS-PAGE results of active fractions obtained using three different columns, as shown in FIG. 1. This result indicates that the VSF protein has a molecular weight of about 163 kDa.

EXAMPLE 16

Analysis of Active Factions Containing VSF Protein by Sucrose Gradient Centrifugation The VSF protein according to the present invention was analyzed by sucrose gradient centrifugation to isolate subunits of the VSF multimer. A linear sucrose gradient (5-55%) was prepared in an ultracentrifuge tube using 5, 10, 20, 25, 42 and 55% sucrose in Tris-HCl. The purified VSF protein was loaded onto the sucrose gradient, and ultracentrifuged at 160,000×g for 16 hrs using SW 41 rotor. After collecting fractions of 1 ml, SDS-PAGE was carried out.

Figure 9:
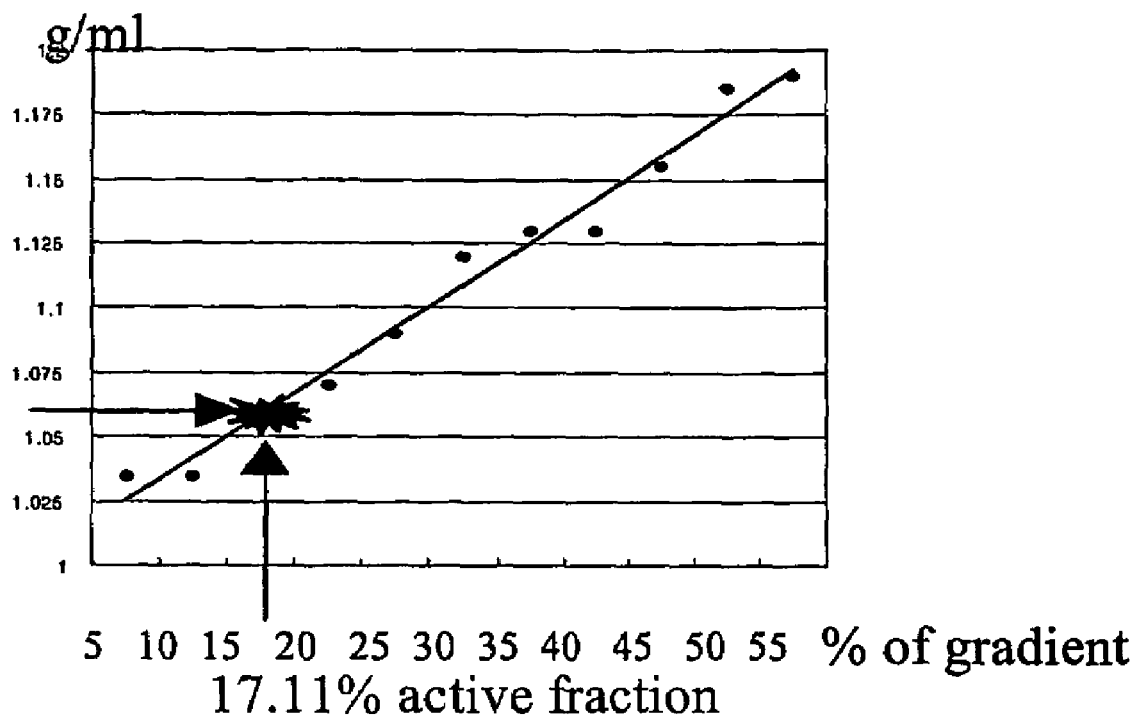
FIG. 9 shows a result of SDS-PAGE of fractions obtained by sucrose gradient centrifugation to identify subunits of a VSF protein according to the present invention (lane 4: fraction obtained in 17.11% sucrose)

As shown in FIG. 9, four major bands were found in the 17.11% sucrose fraction. Herein, a gel filtration marker was used as a standard size marker. The four major bands were identical to major bands of the active fractions obtained using three different columns, as shown in FIG. 1.

EXAMPLE 17

Evaluation for Glycosylation of VSF Protein

Using endoglycosidase H, it was investigated whether the VSF protein is glycosylated.

Endoglycosidase H cleaves bonds between oligosaccharides or polysaccharides and protein by hydrolysis.

The hybridoma 4D1B (accession number KCLRF-BP-00052) prepared in Example 1 was cultured in SFM (serum-free medium, Gibco) at 37° C. under 5% $CO_2$. Thereafter, endoglycosidase H was added to the culture fluid, followed by incubation at 37° C. for 1, 12 and 24 hrs.

Figure 10:
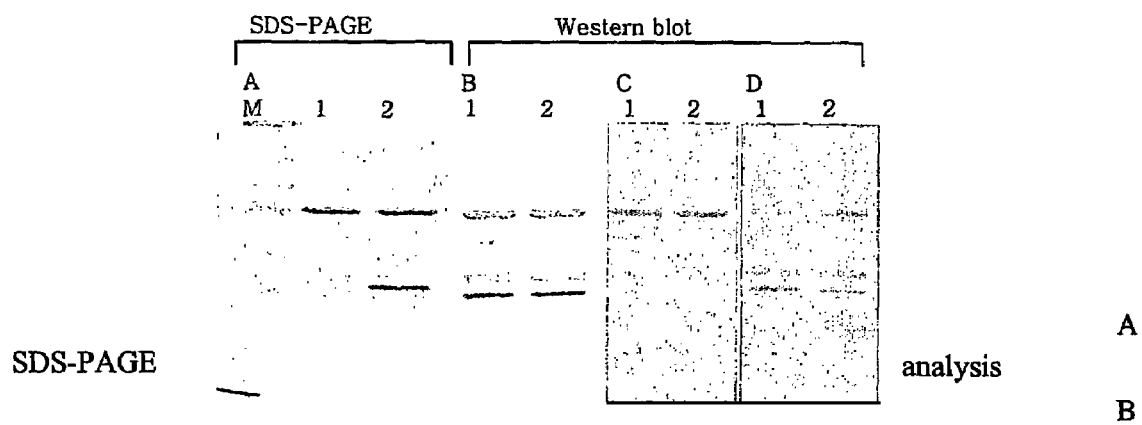
FIG. 10 is a photograph showing results of SDS-PAGE and Western blotting after treatment of a VSF protein according to the present invention with endoglycosidase to investigate glycosylation of the VSF protein (lane 1: purified VSF not treated with endoglycosidase; and lane 2: purified VSF treated with endoglycosidase)
Figure 11A:
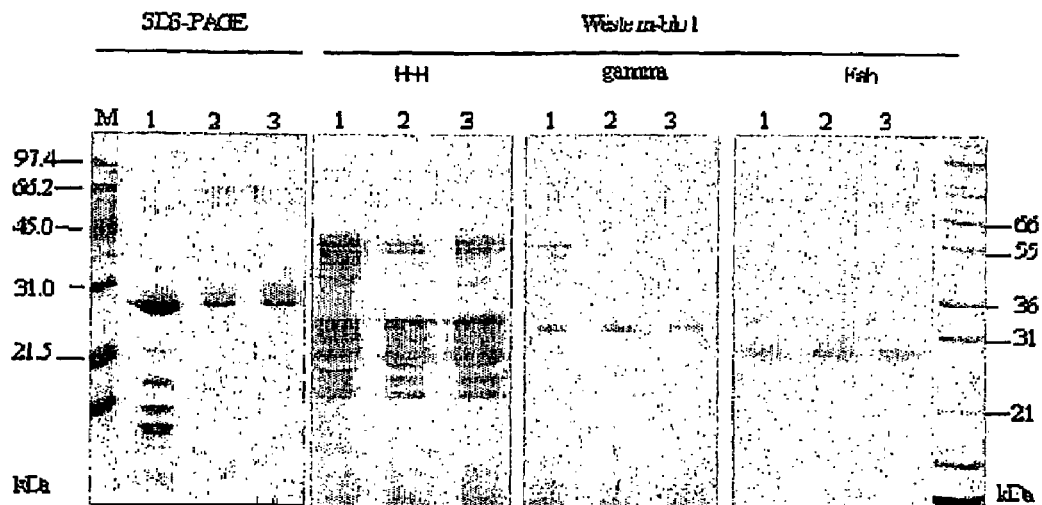
FIGS. 11A to 11D are photographs showing results of SDS-PAGE and Western blotting after treatment of a VSF protein according to the present invention with trypsin, cathepsin, papain and pepsin.
Figure 11A:
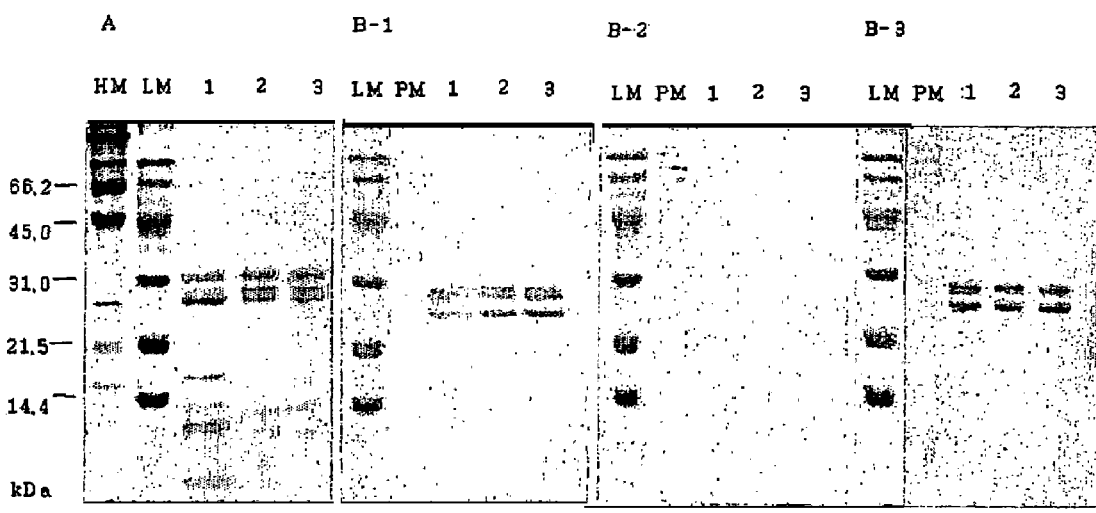
Figure 11B:
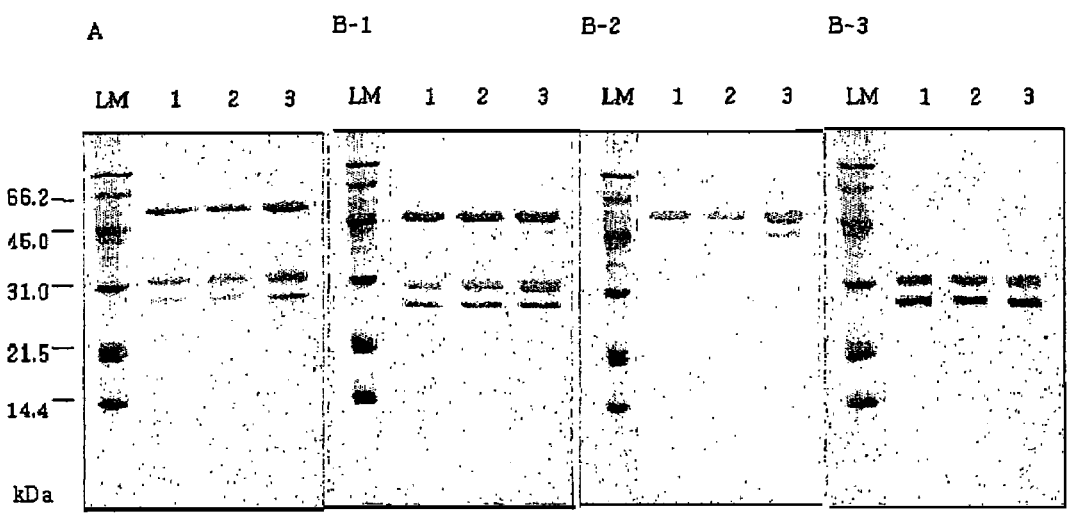
Figure 11C:
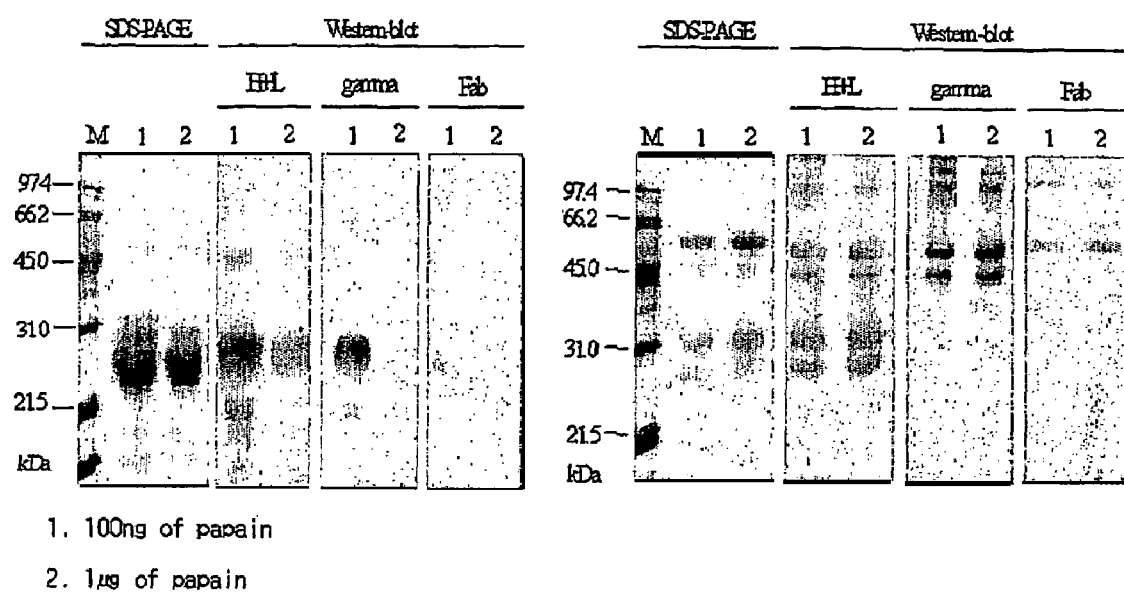
Figure 11D:
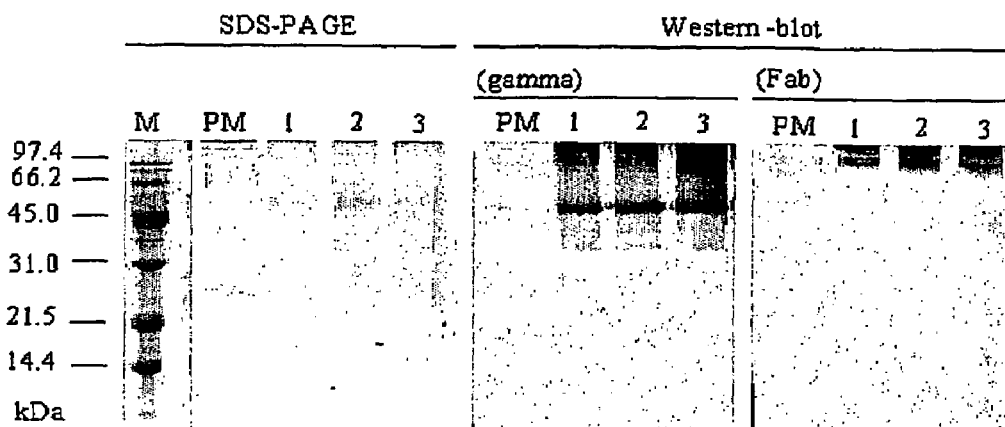
Figure 11D:
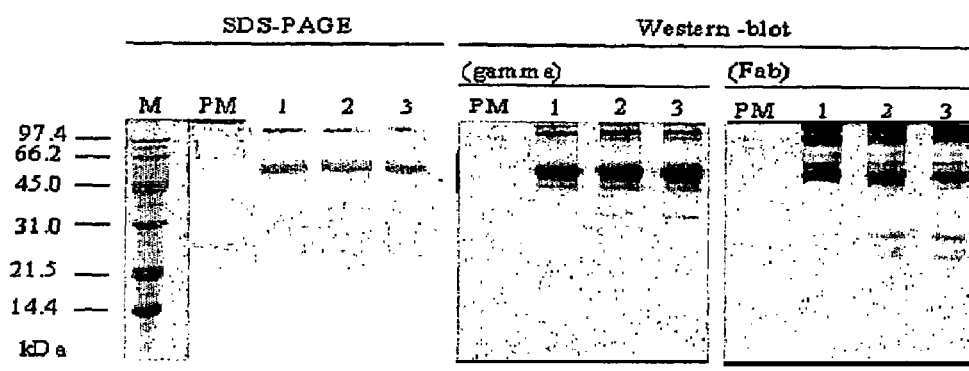

As shown in FIG. 10, when the VSF protein treated with endoglycosidase was separated on a SDS-polyacrylamide gel, there was no band shift. This result indicates that the VSF protein is not glycosylated.

EXAMPLE 18

Evaluation for Sensitivity of VSF Protein to Proteinases

The VSF protein was evaluated for sensitivity to some proteinases. The hybridoma 4D1B (accession number KCLRF-BP-00052) prepared in Example 1 was cultured in SFM (Gibco) at 37° C. under 5% $CO_2$. Trypsin, cathepsin, papain and pepsin were separately added to the culture fluid. Trypsin used in this test had a specific activity of 10,000 BAEE unit/mg protein. 250 µg of trypsin was added to 20 µg of VSF protein, followed by incubation at 37° C. for 1, 6 and 24 hrs. 28 units of cathepsin, which has a specific activity of 33 units/mg protein, was added to 20 µg of VSF protein, followed by incubation at 37° C. for 24, 48 and 72 hrs. Papain was added to 20 µg of VSF protein at various amounts of 100 ng, 1 µg and 5 µg, followed by incubation at 37° C. for 30 min. Pepsin was added to 20 µg of VSF protein at various amounts of 100 ng, 1 µg and 10 µg, followed by incubation at 37° C. for 30 min. After completion of reaction, the culture fluid was analyzed by SDS-PAGE and Western blotting.

As shown in FIGS. 11A to 11D, versus trypsin cleavage, the mouse IgG control showed weak resistance in both light and heavy chains, while the H subunit of the VSF protein was very sensitive, and the L1, L2 and L3 subunits were virtually unaffected by the trypsin treatment. Also, the VSF protein was not cleaved by cathepsin. In case of being treated with papain, the H subunit of the VSF protein and the heavy chain of mouse IgG showed different reactivities to anti-mouse IgG gamma heavy chain. In addition, when compared to the control mouse IgG heavy chain, the H subunit of the VSF protein showed similar susceptibility to pepsin cleavage, but displayed different reactivity to anti-mouse IgG Fab-specific antibody.

These results indicate that the H subunit of the VSF protein is similar to mouse IgG, but the L1, L2 and L3 subunits are very distinct from mouse IgG.

EXAMPLE 19

Evaluation for Heat Stability of VSF Protein

This test was performed to determine a suitable temperature range for long-term storage and use of the VSF protein. The hybridoma 4D1B (accession number KCLRF-BP-00052) prepared in Example 1 was cultured in SFM (Gibco) at 37° C. under 5% $CO_2$. The resulting culture fluid was incubated at 37° C., 56° C. and 65° C. Thereafter, antiviral activity was analyzed by the staining method using crystal violet as described in Example 1.

Figure 12A:
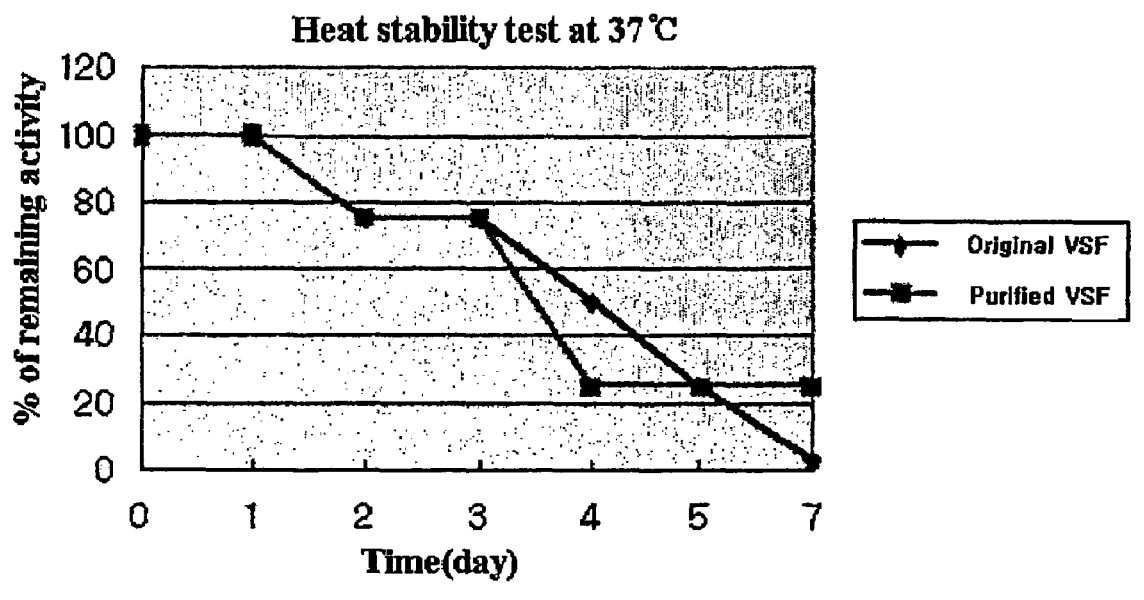
Figure 12B:
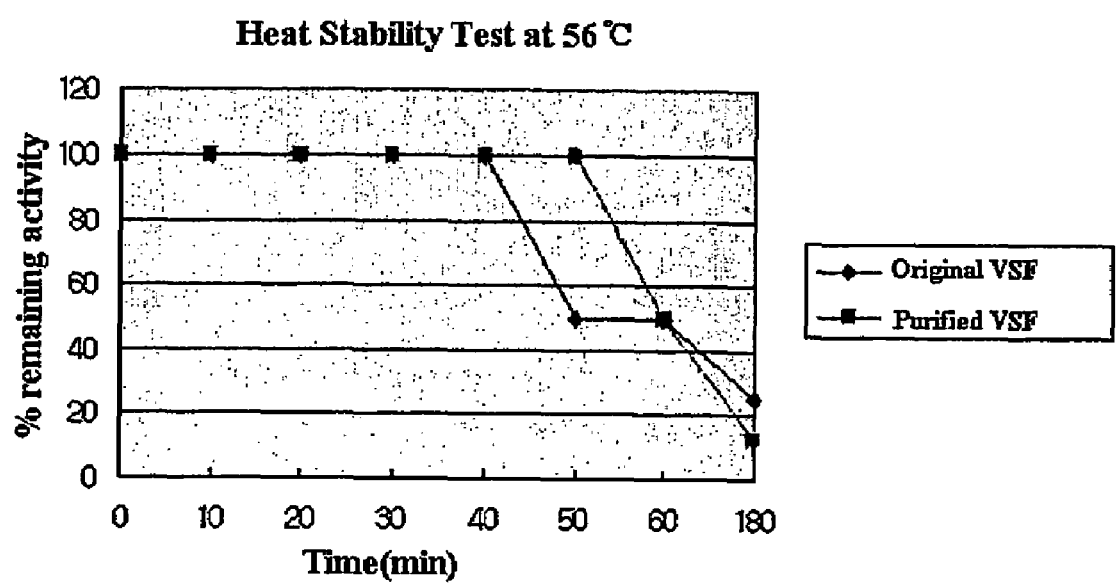

As shown in FIGS. 12A to 12C, the VSF protein contained in the culture fluid was found to be stable for 3 days at 37° C., and about 40 min at 56° C. However, at 65° C., the VSF protein lost over 50% of its antiviral activity within 5 min.

EXAMPLE 20

Evaluation for pH Stability of VSF Protein

This test was performed to determine a suitable pH range for long-term storage and use of the VSF protein. The hybridoma 4D1B (accession number KCLRF-BP-00052) prepared in Example 1 was cultured in SFM (Gibco) at 37° C. under 5% $CO_2$. The resulting culture medium was incubated at a broad range of pH 2.0 to 12.5 for 20 min, 1 hr and 3 hrs. Thereafter, antiviral activity was analyzed by the staining method using crystal violet as described in Example 1. As a result, the VSF protein was found to be stable in a range of pH 7.0 to 8.0.

EXAMPLE 21

Analysis of Primary Structure of VSF Protein

The VSF protein was analyzed for primary structure by MALDI-TOF, N-terminal sequencing and internal sequencing. MALDI-TOF was performed by Genomine, and N-terminal sequencing and Internal sequencing were performed by Korea Basic Science Institute (KBSI), Seoul, Korea. In addition, based on the similarity to mouse immunoglobulin, referring to its known nucleic acid sequences, PCR was carried out to mRNA which was isolated from the hybridoma 4D1B, and, from the resulting amplified products, amino acid sequences were obtained and compared to the amino acid sequences got from MALDI-TOF, N-terminal sequencing and internal sequencing, resulting in finding of genes encoding the H and L3 polypeptides.

As a result, the H polypeptide of the VSF protein was found to have a DNA sequence and an amino acid sequence designated SEQ ID NO: 1 and SEQ ID NO: 2, respectively. The L3 polypeptide was found to have a DNA sequence of SEQ ID NO: 3 and an amino acid sequence of SEQ ID NO: 4. With respect to a result of BLAST search with GeneBank DataBase, as well as molecular weight, amino acid sequence and reactivity to protein A and anti-mouse IgG, the C-termini of the H and L3 polypeptides appear to be identical or very similar to mouse Ig γ3 chain and mouse Ig κ chain, respectively. In addition, the C-termini of the L1 and L2 polypeptide were found to have some amino acid homology with mouse Ig κ chain.

EXAMPLE 22

Analysis of Active Fractions Containing VSF Protein by Western Blotting

The active fractions containing VSF protein prepared in Example 6 were run on a SDS-PAGE gel and analyzed by Western blotting using anti-mouse IgG(H+L) antibody, anti-mouse gamma heavy chain-specific antibody, anti-mouse Fab-specific antibody and anti-mouse kappa light chain-specific antibody.

As a result, when performing Western blotting using anti-mouse IgG(H+L) antibody and anti-mouse Fab-specific antibody, all of four major bands as shown in FIG. 1 were detected. In case of Western blotting with anti-mouse gamma chain-specific antibody, only one band (H) of the four major bands was detected around 55 kDa. In case of Western blotting with anti-mouse kappa light chain-specific antibody, three bands (L1, L2 and L3) were detected around 30 kDa and 25 kDa.

EXAMPLE 23

Evaluation for Inhibitory Activity of VSF Protein Against VSV

The culture fluid of the hybridoma 4D1B secreting VSF protein was evaluated for antiviral activity against VSV (Vesicular Stomatitis Virus). According to the same method as in Example 1, VSV was treated with various dilutions of the culture fluid of the hybridoma 4D1B.

As a result the undiluted culture fluid of the hybridoma 4D1B was found to perfectly suppress proliferation of 100 pfu of VSV. This result supports that the VSF protein has antiviral activity against a variety of viruses.

EXAMPLE 24

Figure 13:
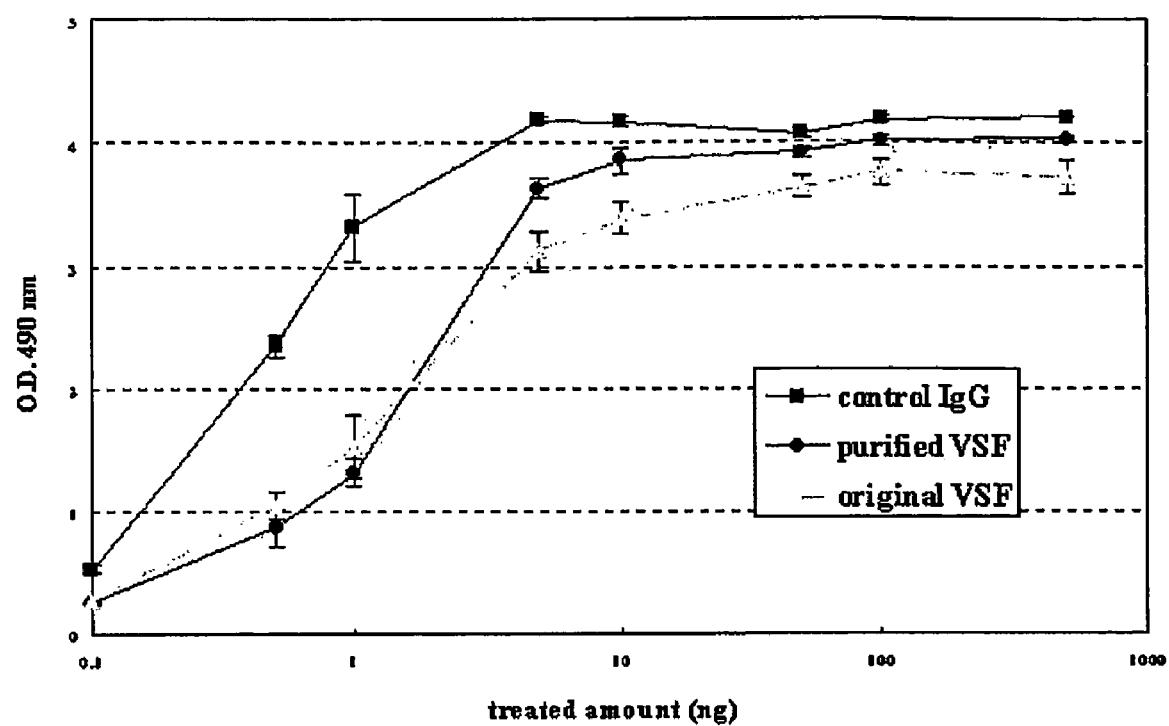
FIG. 13 is a graph showing a result of ELISA, in which reactivity of a VSF protein according to the present invention to anti-mouse IgG(H+L) is compared to that of mouse IgG.

Comparison of Reactivity of VSF Protein and Mouse IgG to Anti-Mouse IgG(H+L) Antibody by ELISA The VSF protein according to the present invention was evaluated for reactivity to anti-mouse IgG, in which mouse IgG was used as a positive control. The culture fluid of the hybridoma 4D1B secreting VSF protein was put into a culture vessel to which anti-mouse IgG was attached in advance, and peroxidase-conjugated anti-mouse IgG was added to the culture vessel. After reaction, optical density was measured at 490 nm. The resulting O.D value was found to be some lower (FIG. 13) than the positive control mouse IgG. This result indicates that the VSF protein contains some components similar to mouse IgG.

---

The invention claimed is:

1. An isolated virus suppressing factor (VSF) protein having the following properties:
   (a) it is increasingly produced in an immune cell stimulated by a variant of encephalomyocarditis virus, EMC-DV;
   (b) it has an antiviral activity which is unchanged by immunoprecipitation and immunoneutralization;
   (c) it is inactivated by proteinase K;
   (d) it is not one of the group of antiviral cytokines consisting of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, G-CSF, GM-CSF, TNF-α, TNF-β, IFN-α, IFN-β, IFN-γ, TGF-β, RANTES, MIP-1α, MIP-1β, MIP-1γ, MCP-1, MCP-3, IP-10 and lymphotactin;
   (e) it comprises about 55 kDa polypeptide (H) having the amino acid sequence of SEQ ID NO: 2, about 30 kDa polypeptides (L1 and L2) and about 25 kDa polypeptide (L3) having the amino acid sequence of SEQ ID NO: 4;
   (f) it has a molecular weight of over about 100 kDa; and
   (g) it is stable at 56° C. for about 40 minutes.

2. The isolated virus suppressing factor (VSF) protein of claim 1, wherein:
   the H polypeptide is encoded by the DNA sequence shown in SEQ ID NO: 1.

3. The isolated VSF protein as set forth in claim 1, wherein the antiviral activity is to suppress proliferation or replication of a virus belonging to the family Orthomyxoviridae, Picornaviridae, Retroviridae or Herpesviridae.

4. A method of producing a hybridoma, comprising fusing an immune cell stimulated by a variant of encephalomyocarditis virus, EMC-DV, with a tumor cell, and producing the hybridoma secreting the isolated virus suppressing factor (VSF) protein of claim 1.

5. A method of preparing the isolated virus suppressing factor (VSF) protein of claim 1, comprising producing a hybridoma secreting the VSF protein by fusing an immune cell stimulated by a variant of encephalomyocarditis virus, EMC-DV, with a tumor cell, culturing the said hybridoma, and isolating the VSF protein from a culture fluid of the said hybridoma.

6. A method of preparing the isolated virus suppressing factor (VSF) protein of claim 1, comprising producing a hybridoma secreting the VSF protein by fusing an immune cell stimulated by a variant of encephalomyocarditis virus, EMC-DV, with a tumor cell, injecting the said hybridoma into an animal, and isolating the VSF protein from an ascitic fluid obtained from the said animal.

7. The method as set forth in claim 5, wherein the VSF protein is isolated from the culture fluid or ascitic fluid using a Blue Sepharose column, a Protein A agarose column, a hydroxyapatite resin column, an FPLC column, or sucrose gradient.

8. A hybridoma producing the isolated virus suppressing factor (VSF) protein of claim 1, which is prepared by fusing an immune cell stimulated by a variant of encephalomyocarditis virus, EMC-DV, with a tumor cell.

9. The hybridoma as set forth in claim 8, wherein the hybridoma is a hybridoma 4D1B (accession number KCLRF-BP-00052).

10. A pharmaceutical composition for treatment of viral infections, comprising a therapeutically effective amount of the VSF protein of claim 1 and a pharmaceutically acceptable carrier.

11. A method of treating vial infections, comprising administering a therapeutically effective amount of the VSF protein of claim 1 to a subject suffering from a viral infection.

12. The method as set forth in claim 6, wherein the VSF protein is isolated from the culture fluid or ascitic fluid using a Blue Sepharose column, a Protein A agarose column, a hydroxyapatite resin column, an FPLC column, or sucrose gradient.

13. The isolated VSF protein of claim 1, wherein the L3 polypeptide is encoded by the DNA sequence shown in SEQ ID NO: 3.

14. The VSF protein of claim 1, wherein the protein is produced by hybridoma 4D1B (accession number KCLRF-BP-00052).

\* \* \* \* \*